US012706185B2

(12) United States Patent
Powers et al.

(10) Patent No.: US 12,706,185 B2
(45) Date of Patent: Aug. 11, 2026

(54) SYSTEMS AND METHODS FOR INDEXING AND SEARCHING HEALTH DATA

(71) Applicant: Truveta, Inc., Bellevue, WA (US)

(72) Inventors: Simon Julian Powers, Seattle, WA (US); Jayaram Nanduri, Issaquah, WA (US); Denesh Singh Pohar, Kirkland, WA (US); Ram Prasad Sunkara, Sammamish, WA (US); Cheuk Wan William Lau, San Francisco, CA (US)

(73) Assignee: Truveta, Inc., Bellevue, WA (US)

(*) Notice: Subject to any disclaimer, the term of this patent is extended or adjusted under 35 U.S.C. 154(b) by 641 days.

(21) Appl. No.: 18/053,540

(22) Filed: Nov. 8, 2022

(65) Prior Publication Data

US 2023/0144503 A1 May 11, 2023

Related U.S. Application Data

(60) Provisional application No. 63/263,733, filed on Nov. 8, 2021, provisional application No. 63/268,995, filed on Mar. 8, 2022.

(51) Int. Cl.
*G06F 17/00* (2019.01)
*G16H 10/60* (2018.01)

(52) U.S. Cl.
CPC .................................. *G16H 10/60* (2018.01)

(58) Field of Classification Search
CPC .............................. G16H 10/60; G16H 50/70
See application file for complete search history.

(56) References Cited

U.S. PATENT DOCUMENTS 7,428,494 B2 9/2008 Hasan et al.
7,827,234 B2 11/2010 Eisenberger et al.
10,534,816 B2 * 1/2020 Gilder .................. G06F 16/215
10,657,613 B2 * 5/2020 Bucur .................... G06Q 10/00
11,151,125 B1 10/2021 Dwivedi et al.
11,295,867 B2 * 4/2022 Oliveira ................ G16H 15/00
(Continued)

FOREIGN PATENT DOCUMENTS

CA 2418239 C 5/2014
CN 101194255 6/2011
(Continued)

OTHER PUBLICATIONS

International Search Report and Written Opinion mailed Feb. 27, 2023, International Application No. PCT/US2022/079455, 19 pages.
(Continued)

*Primary Examiner* — Greta L Robinson
(74) *Attorney, Agent, or Firm* — Workman Nydegger

(57) ABSTRACT

Systems and methods for indexing and searching health data are disclosed herein. In some embodiments, a method for querying patient records includes receiving a search input that specifies a plurality of events, one or more temporal relationships between the events, and inclusion and/or exclusion criteria. An index query is constructed based at least in part on the plurality of events within the search input. The index query is then executed against an inverted index to identify matching patient records. One or more temporal constraints can be solved against the identified patient records. Finally, patient records satisfying the constraint(s) are returned.

31 Claims, 9 Drawing Sheets

(56) References Cited

U.S. PATENT DOCUMENTS 12,057,208 B1 * 8/2024 Esman .................. G16H 20/13
12,086,287 B2 9/2024 Jensen et al.
12,475,257 B2 11/2025 Papel et al.
12,512,193 B2 12/2025 Marcjan et al.
2008/0046292 A1 2/2008 Myers et al.
2008/0306872 A1 12/2008 Felsher
2009/0030290 A1 1/2009 Kozuch et al.
2010/0077006 A1 3/2010 El et al.
2012/0046969 A1 2/2012 Schoenberg
2014/0257045 A1 * 9/2014 Hu ........................ G16H 50/70 600/300
2014/0330578 A1 11/2014 Pincus
2016/0147945 A1 5/2016 MacCarthy et al.
2016/0154978 A1 6/2016 Baker et al.
2016/0210427 A1 7/2016 Mynhier et al.
2017/0103232 A1 4/2017 Scaiano et al.
2017/0161439 A1 6/2017 Raduchel et al.
2018/0089382 A1 3/2018 Allen et al.
2018/0158552 A1 6/2018 Liu et al.
2018/0322946 A1 11/2018 Ika et al.
2019/0034590 A1 1/2019 Oren et al.
2019/0034591 A1 1/2019 Mossin et al.
2019/0057774 A1 2/2019 Velez et al.
2019/0095478 A1 3/2019 Tankersley et al.
2019/0371475 A1 * 12/2019 Oliveira .................. G06N 5/01
2020/0176098 A1 6/2020 Lucas et al.
2020/0276098 A1 9/2020 Nabi et al.
2022/0129584 A1 4/2022 Blackport et al.
2022/0171747 A1 6/2022 Rajyaguru et al.
2022/0222374 A1 7/2022 Antoniou et al.
2023/0147366 A1 5/2023 Marcjan et al.
2023/0148326 A1 5/2023 Papel et al.
2023/0162825 A1 5/2023 Nanduri et al.
2024/0087687 A1 3/2024 Marcjan et al.
2024/0370404 A1 11/2024 Burugapalli et al.
2024/0412830 A1 12/2024 Marcjan et al.
2025/0232063 A1 7/2025 Shinn et al.
2026/0044629 A1 2/2026 Papel et al.

FOREIGN PATENT DOCUMENTS

EP 1994484 3/2015
WO 2007084502 A1 7/2007
WO 2023081909 A1 5/2023
WO 2023081919 A1 5/2023
WO 2023081921 A1 5/2023
WO 2023081921 A8 11/2023

OTHER PUBLICATIONS

Ahmad, Arab , et al., "MDMP: A new algorithm to create inverted index files in BigData, using MapReduce", 2017 7th International Conference on Computer and Knowledge Engineering (ICCKE), IEEE, Oct. 26, 2017 (Oct. 26, 2017), pp. 372-378.

Garfinkel, Simson L., "De-identification of personal information NIST IR 8053", NIST, National Institute of Standards and Technology (NIST), Oct. 21, 2015 (Oct. 21, 2015), pp. 1-54, XP061056032, DOI: 10.6028/NIST.IR.8053.

Sweeney, Latanya , "k-anonymity: a model for protecting privacy k-Anonymity: A Model for Protecting Privacy 1", International Journal on Uncertainty, Oct. 31, 2002 (Oct. 31, 2002), pp. 557-570, XP055268614, URL:https://epic.org/privacy/reidentificat ion/Sweeney Article.pdf [retrieved on Apr. 26, 2016].

Taneja, Himanshu , et al., "Preserving Privacy of Patients Based on Re-identification Risk", Procedia Computer Science, Elsevier, Amsterdam, NL, vol. 70, Nov. 21, 2015, pp. 448-454, XP029309606, ISSN: 187.7-0509, DOI: 10.1016/J.PROCS.2015.10.073.

Uwe, Roth , "A Generalized View on Pseudonyms and Domain Specific Local Identifiers. Lessons Learned from Various Use Cases", The International Journal on Advances in Security, vol. 7, No. 3-4, Dec. 31, 2014 (Dec. 31, 2014), pp. 76-92, XP093019165, ISSN: 1942-2636.

Bodenreider et al., Comparing the Representation of Anatomy in the FMA and Snomed CT, AMIA 2006 Symposium Proceeding, pp. 46-50.

Devlin, Jacob et al., BERT: Pre-training of Deep Bidirectional Transformers for Language Understanding, Proceedings of NAACL-HLT 2019, pp. 4171-4186.

Jimenez-Ruiz et al., Logic-based assessment of the compatibility of UMLS ontology sources, Journal of Biomedical Semantics, 2011, 2(Suppl 1): S2.

Luong et al., Multi-Task Sequence To Sequence Learning, published as a conference paper at ICLR, 2016, 10 pages.

Xue, Linting et al., ByT5: Towards a Token-Free Future with Pre-trained Byte-to-Byte Models, endeavarXiv:2105.13626v3 [cs. CL] Mar. 8, 2022, 16 pages.

Xue, Linting et al., mT5: A Massively Multilingual Pre-trained Text-to-Text Transformer, arXiv:2010.11934v3 [cs. CL] Mar. 11, 2021, 17 pages,.

* cited by examiner

INCLUSION CRITERIA
= R1 & R2 & R3

INDEX QUERY
= (T1 & T2 & (T3|T4) & T4 & T5 & T6) &
(((T13 | T14) & T15) | (((T16 & T17) | T18) & T19) & ((T7 & T8) | (T9 & T10) & (T20 | T21 | T22 | T23))
& (T20 | T21 | T22 | T23) & T11 & T12

SYSTEMS AND METHODS FOR INDEXING AND SEARCHING HEALTH DATA

RELATED APPLICATIONS

This application claims the benefit of U.S. Provisional Patent Application No. 63/263,733, entitled "SYSTEMS AND METHODS FOR INDEXING AND SEARCHING HEALTH DATA," filed on Nov. 8, 2021, and U.S. Provisional Patent Application No. 63/268,995, entitled "SYSTEMS AND METHODS FOR INDEXING AND SEARCHING HEALTH DATA," filed on Mar. 8, 2022, each of which is herein incorporated by reference in its entirety. This application is related to U.S. Provisional Patent Application No. 63/263,725, entitled HEALTH DATA PLATFORM AND ASSOCIATED METHODS, filed on Nov. 8, 2021, U.S. Provisional Patent Application No. 63/263,731, entitled "SYSTEMS AND METHODS FOR DE-IDENTIFYING PATIENT DATA," filed on Nov. 8, 2021, U.S. Provisional Patent Application No. 63/263,735, entitled "SYSTEMS AND METHODS FOR DATA NORMALIZATION," filed on Nov. 8, 2021, U.S. Provisional Patent Application No. 63/268,993, entitled "SYSTEMS AND METHODS FOR QUERYING HEALTH DATA," filed on Mar. 8, 2022, U.S. patent application Ser. No. 18/053,504, entitled "HEALTH DATA PLATFORM AND ASSOCIATED METHODS," filed Nov. 8, 2022, U.S. patent application Ser. No. 18/053,643, entitled "SYSTEMS AND METHODS FOR DE-IDENTIFYING PATIENT DATA," filed with Nov. 8, 2022, and U.S. patent application Ser. No. 18/053,654, entitled "SYSTEMS AND METHODS FOR DATA NORMALIZATION," filed Nov. 8, 2022, each of which is herein incorporated by reference in its entirety.

TECHNICAL FIELD

The present technology generally relates to healthcare, and in particular, to systems and methods for indexing and searching health data.

BACKGROUND

Healthcare entities, such as hospitals, clinics, and laboratories, collect, store and process patient data for payment processing, analytics, and fostering research. While aggregated patient data presents a promising opportunity for researchers and clinicians, searching and analyzing this aggregated data presents several challenges. For example, in the healthcare data domain, it is necessary for entities that handle patient health data to do so in a way that complies with regulations and accepted practices. Additionally, patient data obtained from different entities may be structured according to different formats, include varying levels of detail, different abbreviations or nomenclature, or otherwise differing from one entity to the next, or even within a single entity. Moreover, when dealing with a large corpus of patient data (e.g., millions of patient records), it can be particularly difficult to perform efficient searching to satisfy specified constraints.

Health data can provide valuable insights for research and improving patient care. However, the disclosure and use of certain types of health data are strictly limited by regulations and accepted practices. For example, the Health Insurance Portability and Accountability Act (HIPAA) Privacy Rule imposes stringent protections on protected health information (PHI), defined as individually identifiable health information that is held or transmitted by a HIPAA-covered entity (e.g., healthcare providers, insurers, healthcare clearinghouses) or business associate (e.g., a person or organization that provides certain services to a covered entity). Breaches of PHI can have serious implications on the lives of affected patients, can damage the trust that patients have in their healthcare providers, and can result in severe financial and regulatory penalties for the parties responsible for the breach.

The HIPAA Privacy Rule does not restrict the use or disclosure of de-identified health information—health information that neither identifies nor provides a reasonable basis for identifying a patient or individual. However, conventional techniques for de-identifying health data may remove too much information from the patient record, resulting in data that has limited utility for subsequent applications. Additionally, conventional de-identification techniques may not be well-suited for handling patient data that is received at different times or from different health systems because, for example, they are not stored in a uniform format. Accordingly, improved systems and methods for de-identifying patient data are needed.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1A:
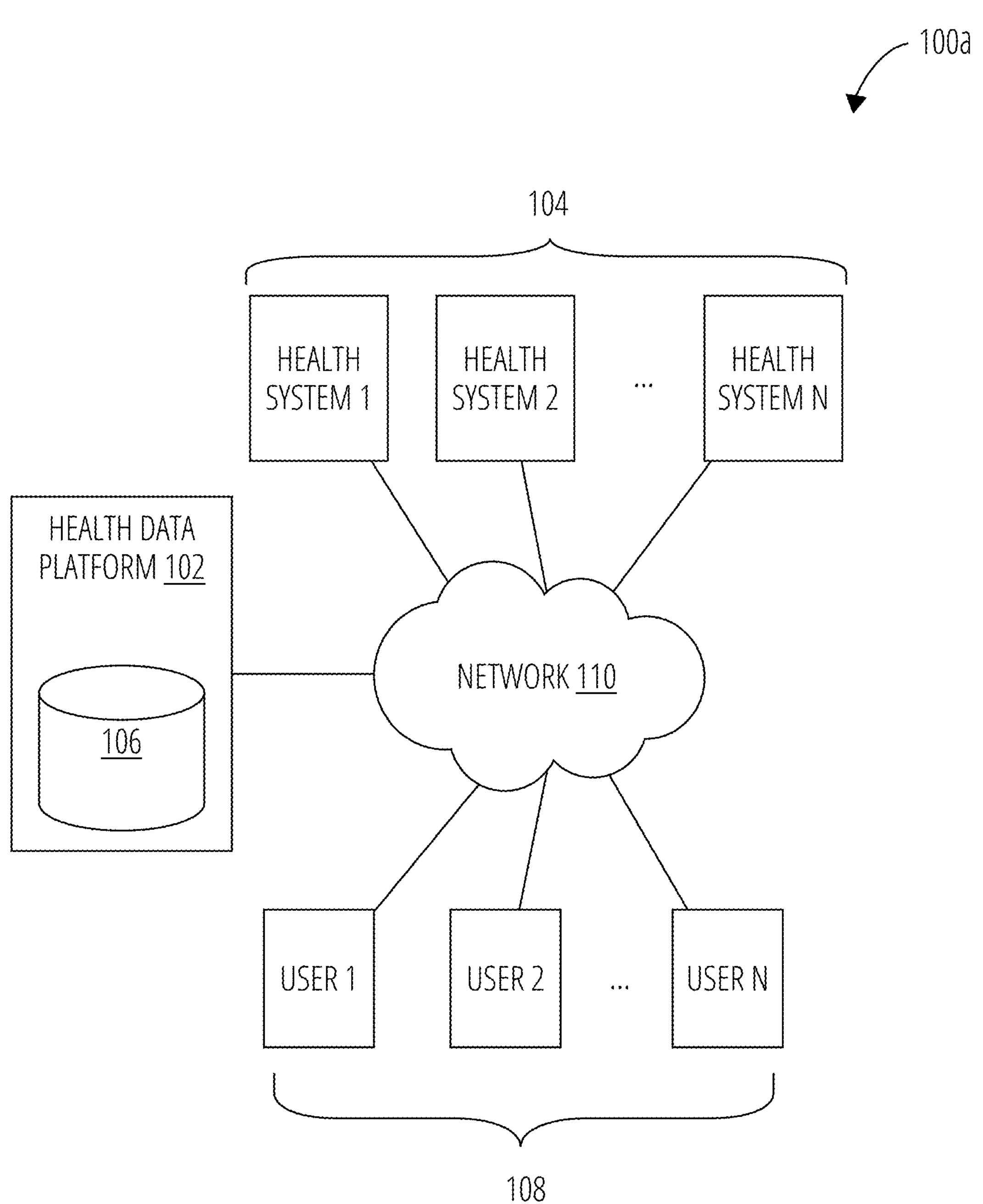
FIG. 1A is a schematic diagram of a computing environment in which a health data platform can operate, in accordance with embodiments of the present technology.

The present technology relates to systems and methods for indexing and searching health data. Health data is often stored in a variety of different formats and supplied by a variety of different entities, such as hospitals, insurance carriers, universities, research institutions, and others. In various embodiments, health data can be aggregated from multiple different sources and converted into a standard format such that search and analysis across the aggregated data is possible. Optionally, the patient data can be de-identified and/or otherwise partially or fully anonymized before being aggregated. In some embodiments, the disclosed techniques provide a network-based patient data management method that acquires and aggregates patient information from various sources into a uniform or common format, stores the aggregated patient information, and notifies health care providers and/or patients, such as after information is updated via one or more communication channels, when new results to a periodic search are available, and so on. In some cases, the acquired patient information may be provided by one or more users through an interface, such as a graphical user interface, that provides remote access to users over a network so that any one or more of the users can provide at least one updated patient record in real time, such as a patient record in a format other than the uniform or common format, including formats that are dependent on a hardware and/or software platform used by a user providing the patient information.

In some instances, aggregated health data can be quite large, for example including hundreds of thousands, millions, or tens of millions of patient records. The health data may be represented by a timeline of events for each patient or patient record, with each event representing an action or change in the patient's medical history (e.g., being diagnosed with a certain condition, having a particular medication administered, etc.).

Researchers and clinicians may wish to query and analyze aggregated health data to identify correlations, trends, causal factors associated with particular outcomes, or any other such relationships. In some examples, a researcher may wish to identify the set of patients that match particular constraints. Those constraints may include temporal aspects (e.g., relative and absolute times of particular events on the patient's timeline), event property values, relationships between events, etc. For example, a query may be intended to find all male patients who were (i) diagnosed with condition C in the last 10 years, (ii) were given medication M within 4 weeks of the diagnosis, and (iii) recorded a lab measurement of type L and score S within 1 year of the diagnosis. Under conventional approaches, this problem might be addressed in multiple stages, for example by defining a Structured Query Language (SQL) query to find candidate patients and then writing a Cassandra Query Language (CQL) query to evaluate those candidate patients. This approach can be cumbersome for researchers and requires familiarity with certain query languages. In real-world situations, a typical query may have up to 300-400 constraints based on the clinical study. Solving such a large number of constraints can be computationally intensive, particularly when applied to hundreds of millions of patients.

In some embodiments, the present technology involves using a single user query to handle such a search request (referred to herein as a "user query" or "primary query"). For example, a user can submit a single query that specifies one or more events (e.g., particular medication administration), one or more relationships between events (e.g., as administration of medication M within 2 months of diagnosis D), as well as one or more exclusion and/or inclusion criteria (e.g., whether a particular patient should be included or excluded in the final result, expressed in terms of the above events or relationships). Based on this single primary query, an index query can be generated that is suitable for querying an inverted index that relates particular index terms to corresponding patient records. Based on the results from the index query, the constraints specified in the primary query can be solved for the returned results to produce final results.

For example, given a data set that includes a number of individual patient timelines that each have one or more events, a single primary query can be created by defining three parameters: (1) sets of events of interest; (2) relationships of interest, defined in terms of the event sets; and (3) inclusion and/or exclusion criteria defined in terms of the relationships of interest. Sets of events of interest can be determined via predicate operations (e.g., all diagnoses on a patient timeline in which a diagnosis code is D and the timestamp is greater than T; or all medication events on a patient timeline in which the medication administrated contains the ingredient I). Relationships of interest can be defined in terms of the temporal or other logical relationships between event sets, such as a situation where an event from Set A is within two weeks of an event from Set B and at least two events from Set C exist before the Set A event. In various examples, these relationships can be dependent on other relationships of interest, and need not be limited only to the initial event sets on the patient timeline. Finally, the inclusion and exclusion criteria can be defined in terms of the relationships, such as finding all patients in which an example of Relationship A and Relationship B can be found, but only if there are no instances of Relationship C.

To execute such a primary query, three steps can be completed: (1) constructing index terms for features generated from patient records; (2) creating an index query to run against an inverted index for patient records having events that match the event sets of interest; and (3) solving the constraints for the patient records returned from the index to determine the final results of the primary query.

In some embodiments, the index can be constructed by using the patient record as the unit of indexing. The different sets of features that can be indexed to retrieve each document may vary and moreover may be dependent on the properties of the patient data and the particular implementation of the index. As described in more detail below, an inverted index mechanism can provide efficient searching at large scale (e.g., tens or hundreds of millions of patient records).

In one approach, an index term can be created for event properties of interest. For example, if a patient has a diagnosis event with a code D, the index term 'diagnosis_code_D' can be stored. Alternatively, if the patient was given medication M intravenously, multiple terms might be stored: 'medication_code_M, medication_iv, medication_code_M_iv'. This would enable the query engine to retrieve this patient record for any event set requiring medication M, or any event set requiring intravenous medication, or any event set requiring medication M given intravenously.

Additionally or alternatively, predicate phrases can be generated for each event, in which the relevant properties for each event are encoded as terms within the phrase. The patient record overall may therefore be represented by a series of phrases. This would allow the query engine to execute queries such as {"diagnosis code D" AND "medication iv"} and ensure that patients returned from the index had individual events matching each of those separate predicate phrases.

In some embodiments, both a forward index and an inverted index can be constructed. The forward index can provide all index terms for a given patient record, while the inverted index can provide all the matching patient records for a given index term. In some examples, the forward index can be divided into multiple sections per patient record, thereby allowing particular parts of the patient record to be retrieved separately (e.g., all events of type T).

To construct the index query, a sequence of steps can be performed. First, the event set predicates can be used to determine the index terms that will match patient records of interest. Second, the identified index terms can be combined together based on relationships specified in the primary query. For example, if Situation A depends on Event Set X and Event Set Y, then the combined index query can be {index terms for X} AND {index terms for Y}. Third, the relationships can be combined together based on the inclusion and exclusion criteria within the query. For example, if the inclusion criteria is 'Situation A OR Situation B,' then the partial queries from those two situations can be combined via an OR operation. Finally, the index query resulting from the preceding steps can be run against the inverted index. These indices are typically very efficient at matching terms with Boolean operators, so this query may be run across a very large corpus of data with low latency.

The results returned from querying the inverted index may have substantially 100% recall, but may have less than 100% precision. This is due to the fact that it is not generally feasible to capture every constraint in an inverted index query. Accordingly, a post-search evaluation step can be performed that handles the constraint solving for each situation.

In some embodiments, the post-search evaluation includes the following sequence of events: (1) retrieving the patient event information from the forward index for each matching patient record; (2) filtering the patient events into the sets specified in the query via the query predicates; (3) solving the constraints for the relationships to determine whether any of them exist on the particular patient timelines; and (4) test the resolved relationships against the inclusion and exclusion criteria specified in the primary query and return the patient records that match (i.e., inclusion if true and exclusion if false). For solving the situational constraints, any number of optimized constraint solving techniques may be deployed (e.g., a backtracking search).

Although many examples described herein relate to health data, and to patient records in particular, embodiments of the present technology can be applied to indexing, searching, and analyzing any suitable data type. Some embodiments can be particularly useful for indexing and searching data that has a temporal component, whether that data can be represented as a timeline of events or is otherwise structured to incorporate temporal information.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The headings provided herein are for convenience only and do not interpret the scope or meaning of the claimed present technology. Embodiments under any one heading may be used in conjunction with embodiments under any other heading.

I. Health Data Platform

Figure 1B:
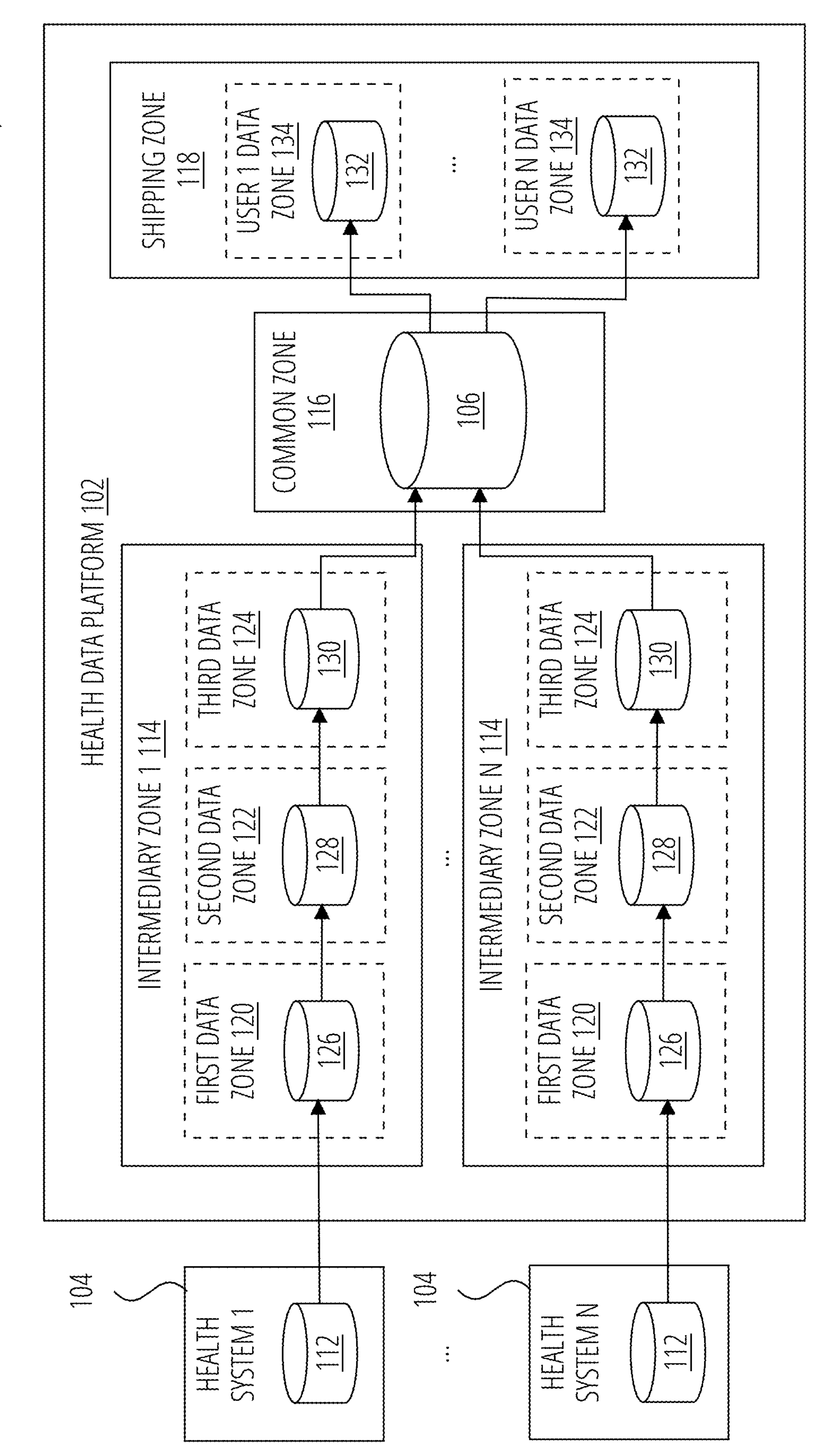
FIG. 1B is a schematic diagram of a data architecture that can be implemented by a health data platform, in accordance with embodiments of the present technology.

FIGS. 1A and 1B provide a general overview of a health data platform configured in accordance with embodiments of the present technology. Specifically, FIG. 1A is a schematic diagram of a computing environment 100*a* in which a health data platform 102 can operate, and FIG. 1B is a schematic diagram of a data architecture 100*b* that can be implemented by the health data platform 102.

Referring first to FIG. 1A, the health data platform 102 is configured to receive health data from a plurality of health systems 104, aggregate the health data into a common data repository 106, and allow one or more users 108 to access the health data stored in the common data repository 106. As described in further detail below, the common data repository 106 can store health data from multiple different health systems 104 and/or other data sources in a uniform schema, thus allowing for rapid and convenient searching, analytics, modeling, and/or other applications that would benefit from access to large volumes of health data.

The health data platform 102 can be implemented by one or more computing systems or devices having software and hardware components (e.g., processors, memory) configured to perform the various operations described herein. For example, the health data platform 102 can be implemented as a distributed "cloud" server across any suitable combination of hardware and/or virtual computing resources. The health data platform 102 can communicate with the health system 104 and/or the users 108 via a network 110. The network 110 can be or include one or more communications networks, such as any of the following: a wired network, a wireless network, a metropolitan area network (MAN), a local area network (LAN), a wide area network (WAN), a virtual local area network (VLAN), an internet, an extranet, an intranet, and/or any other suitable type of network or combinations thereof.

The health data platform 102 can be configured to receive and process many different types of health data, such as patient data. Examples of patient data include, but are not limited to, the following: age, gender, height, weight, demographics, symptoms (e.g., types and dates of symptoms), diagnoses (e.g., types of diseases or conditions, date of diagnosis), medications (e.g., type, formulation, prescribed dose, actual dose taken, timing, dispensation records), treatment history (e.g., types and dates of treatment procedures, the healthcare facility or provider that administered the treatment), vitals (e.g., body temperature, pulse rate, respiration rate, blood pressure), laboratory measurements (e.g., complete blood count, metabolic panel, lipid panel, thyroid panel, disease biomarker levels), test results (e.g., biopsy results, microbiology culture results), genetic data, diagnostic imaging data (e.g., X-ray, ultrasound, MRI, CT), clinical notes and/or observations, other medical history (e.g., immunization records, death records), insurance information, personal information (e.g., name, date of birth, social security number (SSN), address), familial medical history, and/or any other suitable data relevant to a patient's health. In some embodiments, the patient data is provided in the form of electronic health record (EHR) data, such as structured EHR data (e.g., schematized tables representing orders, results, problem lists, procedures, observations, vitals, microbiology, death records, pharmacy dispensation records, lab values, medications, allergies, etc.) and/or unstructured EHR data (e.g., patient records including clinical notes, pathology reports, imaging reports, etc.). A set of patient data relating to the health of an individual patient may be referred to herein as a "patient record."

The health data platform 102 can receive and process patient data for an extremely large number of patients, such as thousands, tens of thousands, hundreds of thousands, millions, tens of millions, or hundreds of millions of patients. The patient data can be received continuously, at predetermined intervals (e.g., hourly, daily, weekly, monthly), when updated patient data is available and/or pushed to the health data platform 102, in response to requests sent by the health data platform 102, or suitable combinations thereof. Thus, due to the volume and complexity of the patient data involved, many of the operations performed by the health data platform 102 are impractical or impossible for manual implementation.

Optionally, the health data platform 102 can also receive and process other types of health data. For example, the health data can also include facility and provider information (e.g., names and locations of healthcare facilities and/or providers), performance metrics for facilities and providers (e.g., bed utilization, complication rates, mortality rates, patient satisfaction), hospital formularies, health insurance claims data (e.g., 835 claims, 837 claims), supply chain data (e.g., information regarding suppliers of medical devices and/or medications), device data (e.g., device settings, indications for use, manufacturer information, safety data), health information exchanges and patient registries (e.g., immunization registries, disease registries), research data, regulatory data, and/or any other suitable data relevant to healthcare. The additional health data can be received continuously, at predetermined intervals (e.g., hourly, daily, weekly, monthly), as updated data is available, upon request by the health data platform 102, or suitable combinations thereof.

The health data platform 102 can receive patient data and/or other health data from one or more health systems 104. Each health system 104 can be an organization, entity, institution, etc., that provides healthcare services to patients. A health system 104 can optionally be composed of a plurality of smaller administrative units (e.g., hospitals, clinics, labs, or groupings thereof), also referred to herein as "care sites." The health data platform 102 can receive data from any suitable number of health systems 104, such as one, two, four, five, ten, fifteen, twenty, thirty, forty, fifty, hundreds, or thousands or more different health systems 104. Each health system 104 can include or otherwise be associated with at least one computing system or device (e.g., a server) that communicates with the health data platform 102 to transmit health data thereto. For example, each health system 104 can generate patient data for patients receiving services from the respective health system 104, and can transmit the patient data to the health data platform 102. As another example, each health system 104 can generate operational data relating to the performance metrics of the care sites within the respective health system 104, and can transmit the operational data to the health data platform 102.

Optionally, the health data platform 102 can receive health data from other data sources besides the health systems 104. For example, the health data platform 102 can receive health data from one or more databases, such as public or licensed databases on drugs, diseases, medical ontologies, demographics and/or other patient data, etc. (e.g., SNOMED CT, RxNorm, ICD-10, FHIR, LOINC, UMLS, OMOP, LexisNexis, state vaccine registries). In some embodiments, this additional health data provides metadata that is used to process, analyze, and/or enhance patient data received from the health systems 104, as described below.

The health data platform 102 can perform various data processing operations on the received health data, such as de-identifying health data that includes patient identifiers, converting the health data from a health system-specific format into a uniform format, and/or enhancing the health data with additional data. Subsequently, the health data platform 102 can aggregate the processed health data in the common data repository 106. The common data repository 106 can be or include one or more databases configured to store health data from multiple health systems 104 and/or other data sources. The health data in the common data repository 106 can be in a uniform schema or format to facilitate downstream applications. For example, the health data platform 102 performs additional data processing operations on the health data in the common data repository 106, such as analyzing the health data (e.g., using machine learning models and/or other techniques), indexing or otherwise preparing the health data for search and/or other applications, updating the health data as additional data is received, and/or preparing the health data for access by third parties (e.g., by performing further de-identification processes). Additional details of some of the operations that can be performed by the health data platform 102 are described below with respect to FIG. 1B.

The health data platform 102 can allow one or more users 108 (e.g., researchers, healthcare professionals, health system administrators) to access the aggregated health data stored in the common data repository 106. Each user 108 can communicate with the health data platform 102 via a computing device (e.g., personal computer, laptop, mobile device, tablet computer) and the network 110. For example, a user 108 can send a request to the health data platform 102 to retrieve a desired data set, such as data for a population of patients meeting one or more conditions (e.g., diagnosed with a particular disease, receiving particular medication, belonging to a particular demographic group). The health data platform 102 can search the common data repository 106 to identify a subset of the stored health data that fulfills the requested conditions, and can provide the identified subset to the user 108. Optionally, the health data platform 102 can perform additional operations on the identified subset of health data before providing the data to the user, such as de-identification and/or other processes to ensure data security and patient privacy protection.

FIG. 1B illustrates the data architecture 100*b* of the health data platform 102, in accordance with embodiments of the present technology. The health data platform 102 can be subdivided into a plurality of discrete data handling zones, also referred to herein as "zones" or "domains." Each zone is configured to perform specified data processing operations and store the data resulting from such operations. For example, in the illustrated embodiment, the health data platform 102 includes a plurality of intermediary zones 114 (also known as "embassies") that receive and process health data from the health systems 104, a common zone 116 that aggregates the data from the intermediary zones 114 in the common data repository 106, and a shipping zone 118 that provides selected data for user access. Each zone can include access controls, security policies, privacy rules, and/or other measures that define data isolation boundaries tailored to the sensitivity level of the data contained within that zone. The flow of data between zones can also be strictly controlled to mitigate the risk of privacy breaches and/or other data security risks.

In the illustrated embodiment, each of the health systems 104 includes at least one health system database 112. The health system database 112 can store health data produced by the respective health system 104, such as patient data for the patients receiving healthcare services from the health system 104, operational data for the health system 104, etc. The patient data stored in the health system database 112 can include or be associated with identifiers such as the patient's name, address (e.g., street address, city, county, zip code), relevant dates (e.g., date of birth, date of death, admission date, discharge date), phone number, fax number, email address, SSN, medical record number, health insurance beneficiary number, account number, certificate or license number, vehicle identifiers and/or serial numbers (e.g., license plate numbers), device identifiers and/or serial numbers, web URL, IP address, finger and/or voice prints, photographic images, and/or any other characteristic or information that could uniquely identify the patient. Accordingly, the patient data can be considered to be PHI (e.g., electronic PHI (ePHI)), which may be subject to strict regulations on disclosure and use.

As shown in FIG. 1B, health data can be transmitted from the health systems 104 to the health data platform 102 via respective secure channels and/or over a communications network (e.g., the network 110 of FIG. 1A). The health data can be transmitted continuously, at predetermined intervals, in response to pull requests from the health data platform 102, when the health systems 104 push data to the health data platform 102, or suitable combinations thereof. For example, some or all of the health systems 104 can provide a daily feed of data to the health data platform 102.

The health data from the health systems 104 can be received by the intermediary zones 114 of the health data platform 102. In some embodiments, the intermediary zones 114 are configured to process the health data from the health systems 104 to prepare the data for aggregation in the common zone 116. For example, each intermediary zone 114 can de-identify the received health data to remove or otherwise obfuscate identifying information so that the health data is no longer classified as PHI and can therefore be aggregated and used in a wide variety of downstream applications (e.g., search, analysis, modeling). The intermediary zone 114 can also normalize the received health data by converting the data from a health system-specific format to a uniform format suitable for aggregation with health data from other health systems 104. As shown in FIG. 1B, each intermediary zone 114 can receive health data from a single respective health system 104. The intermediary zones 114 can be isolated from each other such that health data across different health systems 104 cannot be combined with each other or accessed by unauthorized entities (e.g., a health system 104 other than the health system 104 that originated the data) before patient identifiers have been removed.

In the illustrated embodiment, each intermediary zone 114 includes a plurality of data zones that sequentially process the health data from the respective health system 104. For example, in the illustrated embodiment, each intermediary zone 114 includes a first data zone 120 (also known as a "landing zone"), a second data zone 122 (also known as an "enhanced PHI zone"), and a third data zone 124 (also known as an "enhanced DeID zone").

As shown in FIG. 1B, the health data from each health system 104 can initially be received and processed by the first data zone 120 (landing zone). The first data zone 120 can implement one or more data ingestion processes to extract relevant data and/or filter out erroneous or irrelevant data. The data ingestion processes can be customized based on the particular health system 104, such as based on the data types and/or formats produced by the health system 104. Accordingly, the first data zones 120 within different intermediary zones 114 can implement different data ingestion processes, depending on the particular data output of the corresponding health system 104. The data resulting from the data ingestion processes can be stored in a first database 126 within the first data zone 120. The data can remain in the first database 126 indefinitely or for a limited period of time (e.g., no more than 30 days, no more than 1 year, etc.), e.g., based on the preferences of the respective health system 104, security considerations, and/or other factors. The data in the first database 126 can still be considered PHI because the patient identifiers have not yet been removed from the data. Accordingly, the first data zone 120 can be subject to relatively stringent access controls and data security measures.

The data produced by the first data zone 120 can be transferred to the second data zone 122 (enhanced PHI zone). In some embodiments, the data received from the first data zone 120 is initially in a non-uniform format, such as a format specific to the health system 104 that provided the data. Accordingly, the second data zone 122 can implement one or more data normalization processes to convert the data into a unified, normalized format or schema (e.g., a standardized data model). Optionally, data normalization can include enhancing, enriching, annotating, or otherwise supplementing the health data with additional data (e.g., health metadata received from databases and/or other data sources). The data resulting from these processes can be stored in a second database 128 within the second data zone 122. The data can remain in the second database 128 indefinitely or for a limited period of time (e.g., no more than 30 days, 1 year, etc.), e.g., based on the preferences of the respective health system 104, security considerations, and/or other factors. The data stored in the second database 128 can still be considered PHI because the patient identifiers have not yet been removed from the data. Accordingly, the second data zone 122 can also be subject to relatively stringent access controls and data security measures, similar to the first data zone 120.

The data produced by the second data zone 122 can be transferred to the third data zone 124 (enhanced DeID zone). The third data zone 124 can implement one or more de-identification processes to remove and/or modify identifiers from the data so that the data is no longer classified as PHI. The de-identification processes can include, for example, modifying the data to remove, alter, coarsen, group, and/or shred patient identifiers, and/or removing or suppressing certain patient records altogether. For example, a patient record can be suppressed if the record would still potentially be identifiable even after the identifiers have been removed and/or modified (e.g., if the record shows a diagnosis of an extremely rare disease). In some embodiments, the de-identification processes also include producing tokens that allow data from the same patient to be tracked without using the original identifiers. The resulting de-identified data can be stored in a third database 130 within the third data zone 124. The data can remain in the third database 130 indefinitely or for a limited period of time (e.g., no more than 30 days, 1 year, etc.), e.g., based on the preferences of the respective health system 104, security considerations, and/or other factors. Because the data stored in the third database 130 is no longer considered PHI, the third data zone 124 can have less stringent access controls and data security measures than the first and second data zones 120, 122.

The de-identified data produced by each intermediary zone 114 can be transferred to a common zone 116 within the health data platform 102 via respective secure channels. The common zone 116 can include the common data repository 106 that stores aggregated health data from all of the health systems 104. As discussed above, the data stored in the common data repository 106 has been de-identified and/or normalized into a uniform schema, and can therefore be used in many different types of downstream applications. For example, the common zone 116 can implement processes that analyze the data in the common data repository 106 using machine learning and/or other techniques to produce various statistics, analytics (e.g., cohort analytics, time series analytics), models, knowledge graphs, etc. As another example, the common zone 116 can implement processes that index the data in the common data repository 106 to facilitate search operations.

The data stored in the common data repository 106 can be selectively transferred to the shipping zone 118 of the health data platform 102 for access by one or more users 108 (not shown in FIG. 1B). In the illustrated embodiment, the shipping zone 118 includes a plurality of user data zones 134. Each user data zone 134 can be customized for a particular user 108, and can store and expose a selected subset of data for access by that user 108. The user data zones 134 can be isolated from each other so that each user 108 can only access data within their assigned user data zone 134. The amount, type, and/or frequency of data transferred to each user data zone 134 can vary depending on the data requested by the user 108 and the risk profile of the user 108. For example, the user 108 can send a request to the health data platform 102 (e.g., via the network 110 of FIG. 1A) for access to certain data in the common data repository 106 (e.g., data for patients who have been diagnosed with a particular disease, belong to a particular population, have received a particular treatment procedure, etc.). The common zone 116 can implement a search process to identify a subset of the data in the common data repository 106 that fulfills the request parameters. Optionally, depending on the risk profile of the user 108, the common zone 116 can perform additional de-identification processes and/or apply other security measures to the identified data subset. The identified data subset can then be transferred to the user data zone 134 for access by the user 108 (e.g., via a secure channel in the network 110 of FIG. 1A). Additional details regarding indexing and search of data within the user data zones 134 are described below in Sections II and III.

The data architecture 100*b* illustrated in FIG. 1B can be configured in many different ways. For example, although the intermediary zones 114 are illustrated in FIG. 1B as having three data zones, in other embodiments, some or all of the intermediary zones 114 can include fewer or more data zones. Any of the zones illustrated in FIG. 1B can alternatively be combined with each other into a single zone, or can be subdivided into multiple zones. Any of the processes described herein as being implemented by a particular zone can instead be implemented by a different zone, or can be omitted altogether.

II. Methods for Indexing Health Data

Indices can be usefully employed to facilitate searching health data, particularly in instances involving a very large corpus of data (e.g., tens of millions of patient records). As described in more detail below, some embodiments of the present technology relate to generating an inverted index and/or a forward index for particular terms or phrases within patient records.

Figure 2:
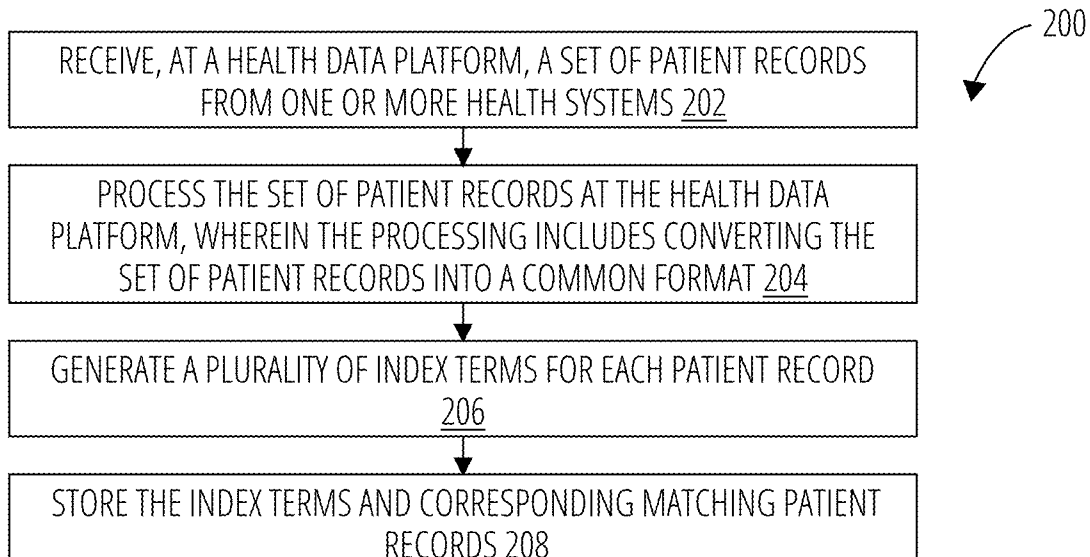
FIG. 2 illustrates an example routine for indexing patient records in accordance with embodiments of the present technology.

FIG. 2 illustrates an example routine 200 for indexing patient records. In block 202, routine 200 receives, at a health data platform, a set of patient records from one or more health systems. As described previously, in some embodiments the patient records received from various health systems can be aggregated. Alternatively, the set of patient records may all originate from a single health system. In block 204, routine 200 processes the set of patient records at the health data platform, wherein the processing includes converting the set of patient records into a common format. For example, a normalization process can be utilized to convert the data into a unified, normalized format or schema (e.g., a standardized data model). Optionally, data normalization can include enhancing, enriching, annotating, or otherwise supplementing the health data with additional data. Additionally or alternatively, the patient records can be de-identified, and/or otherwise processed via the health data platform to facilitate downstream analysis and to protect patient confidentiality.

In block 206, routine 200 generates a plurality of index terms for each patient record. As used herein, index terms can be words or phrases corresponding to particular events or attributes (e.g., medical events such as diagnoses, medication administrations, etc., or attributes such as patient age, sex, etc.). In block 208, routine 200 stores the index terms and corresponding matching patient records in an index file such as a posting list. Posting lists are used by search indices to quickly search for documents containing specific terms. As illustrated in the example below, the posting list can include all the unique terms from a set of documents. These terms can be stored in sorted order, with each term having a list of corresponding document identities that contain the term.

| Term | Matching Documents |
|---|---|
| Diagnosis_1 | 6, 780, 1040, 3890, 5430, 67445, . . . |
| . . . | |
| Diagnosis_45 | 2045, 6078, 15064, 61890, . . . |
| Diagnosis_46 | 857, 5673, 9932, . . . |
| . . . | |
| Diagnosis_87 | 12, 56, 98, 260, 350, 705, 906, 967, . . . 2024, 2045, 2079, 2116, . . . 6078, 7098, . . . |
| Diagnosis_88 | 98, 2045, 3056, 8080, 10356, . . . |
| . . . | |

As its simplest, this allows very efficient answers to queries like "Return all documents with the term {Diagnosis_1}." In this case it is documents numbered 6, 780, 1040, etc. This approach also allows very efficient queries using Boolean logic like {termX AND (termY OR termZ)}. For example, consider the query {Diagnosis_45 AND Diagnosis_87} when executed against the above posting lists. The first document in each posting list is 2045 (Diagnosis_45) and 12 (Diagnosis_87). The retrieval process now knows that it need not consider any document numbered less than 2045, as none of them contain the term "Diagnosis_45." The process can therefore skip rapidly through the posting list for "Diagnosis_87" until it gets to a document number equal to or greater than 2045. Well known techniques exist (e.g., skip lists) to allow the retrieval process to perform this forward search without considering every entry in the posting list. In this case document 2045 contains both the term "Diagnosis_45" and "Diagnosis_87" and so it becomes the first document to satisfy the query.

In some embodiments, the data in posting lists can be enhanced with more than just the document number. For example, one approach to support phrasal type queries is to also store the position of the term within the document as part of the posting. This is shown below as (doc #, term position).

| Term | Matching Documents |
|---|---|
| Diagnosis_1 | (6, 57), (6, 203), (780, 103), (1040, 1), (3890, 567), (5430, 34), . . . |
| . . . | |
| Diagnosis_45 | (2045, 45), (6078, 67), (15064, 438), (61890, 203), . . . |

-continued

| Term | Matching Documents |
|---|---|
| Diagnosis_46 | (857, 34), (5673, 872), (9932, 539), . . . |
| . . . | |
| Diagnosis_87 | (12, 6), (56, 227), . . . (2024, 24), (2045, 98), (2079, 89), . . . (6078, 68), (7098, 104) . . . |
| Diagnosis_88 | (98, 2), (2045, 87), (3056, 7), (8080, 456), (10356, 205), . . . |
| . . . | |

In this case the simple query {Diagnosis_45 AND Diagnosis_87} would match documents 2045 and 6078, since they both contain those two terms. However, the phrasal query {““Diagnosis_45 Diagnosis)87”}—where the quotes are used to indicate a phrase search—would only match document 6078. That has the terms adjacent and in the correct order (positions 67 and 68), while in document 2045 they are in different parts of the text (positions 45 and 98).

Applying this approach to health data such as patient records, index terms can be generated for each patient record. In some embodiments, the index terms can correspond directly to simple terms within the patient record (e.g., a medication). Additionally or alternatively, artificial terms can be generated based on the patient record. For example, to record particular diagnoses, different types of conditions can be encoded in a concept code (e.g., an integer value, an alphabetical identifier, an alphanumeric identifier, etc.). An example of such a posting list with numerical concept codes is shown below.

| Term | Matching Documents |
|---|---|
| Diagnosis_1 | 6, 780, 1040, 3890, 5430, 67445, . . . |
| . . . | |
| Diagnosis_45 | 2045, 6078, 15064, 61890, . . . |
| Diagnosis_46 | 857, 5673, 9932, . . . |
| . . . | |
| Diagnosis_87 | 12, 56, 98, 260, 350, 705, 906, 967, . . . 2024, 2045, 2079, 2116, . . . 6078, 7098, . . . |
| Diagnosis_88 | 98, 2045, 3056, 8080, 10356, . . . |
| . . . | |

Using this index and the techniques previously described, a search query can quickly find patients with a particular combination of conditions indicated on the patient records. For example, {Diagnosis_45 AND Diagnosis_87} will return the patient record 2045.

In a patient record, the position of the term in the document may be relatively unimportant. However, the time of the diagnosis (or other event) may be highly relevant. In some embodiments, the time can be represented as a position along a patient timeline. For example, the timeline position of each diagnosis term can be encoded as a "days since birth" value or as time since or before any particular reference event. In the example below, patient 6 was given "Diagnosis 1" on the 57th day after she was born.

| Term | Matching Documents |
|---|---|
| Diagnosis_1 | (6, 57), (780, 1030), (1040, 14043), (3890, 567), (5430, 12894), . . . |
| . . . | |
| Diagnosis_45 | (2045, 8467), (6078, 1334), (15064, 438), (61890, 20363), . . . |
| Diagnosis_46 | (857, 19002), (5673, 8720), (9932, 26549), . . . |
| . . . | |
| Diagnosis_87 | (12, 60), (56, 227) . . . (2024, 2), (2045, 98), (2079, 8900) . . . (6078, 1402), (7098, 104) . . . |
| Diagnosis_88 | (98, 2), (2045, 87), (3056, 7), (8080, 456), (10356, 205), . . . |
| . . . | |

By encoding temporal attributes in an inverted index, a retrieval process can quickly execute queries such as "Find all patients diagnosed with condition 46 aged over 50." In the above example, this corresponds to the posting list for Diagnosis_46 where term position is greater than 18,250 (50*365), resulting in the identification of patient records 857 and 9932. Although in this simplified example a year is characterized as 365 days (and therefore disregards leap years), even with this discrepancy the search would simply return some patients who were slightly under 50 years old. The small number of discrepancies may then be filtered out in subsequent steps. In some embodiments, the index and query can be constructed so as to minimize returning patient records that cannot possibly satisfy the query, while returning all patient records that do satisfy the query, even if some false positives are also returned.

Using an inverted index with temporal encoding allows for filtering based on relative constraints between terms. Consider the query "Find patients diagnosed with condition 87 sometime after diagnosis 45." In the posting list above, patient records 2045 and 6078 both include these diagnoses recorded against them, but only 6078 meets the relative time constraint (day 1334 for diagnosis 45 and day 1402 for diagnosis 87).

In some embodiments, with appropriate customization of the query operators and posting lists, operators such as "before," "after," "within n days," "ordered," and "separated by n days" may all be implemented. This approach allows very efficient filtering to increase the precision of the set of patient records returned. For example, a query operator "before" can be used support queries like {Diagnosis_4 before Diagnosis_12}. An operator such as within(n) can be used to test whether terms are close enough together in the timeline space. For example, the query {Medication_12 within(6) Diagnosis_15} would only match patients where those indexed terms are separated by less than 6 "positions" or events in a patient timeline.

In some embodiments, this approach can be extended to storing events such as like lab result values, vitals measurements (weight, blood pressure, etc.), risk scores, etc. For example, an index posting format for lab results may take the form of: "#patient doc, #days since birth when recorded, #normalized lab value." This approach enables efficient searches for patients with a certain lab measurement, with an optional age filter and an optional min/max/range value. Optionally, this can be combined via Boolean logic as described above to solve relatively complex constraints at the index lookup level (e.g., identify patients given medication M, followed by Diagnosis D within T days, followed sometime after by a lab measurement type L where the value is between X and Y).

As described in more detail below, to facilitate efficient searching of the inverted index, the query language utilized by a user submitting a primary search query may be expressed in terms of constraints between events on a patient record (e.g., events along a patient timeline). This primary query may then be transformed into an index query that can be run against the inverted index. This approach has at least two significant advantages. First, this permits leveraging of many of the optimizations and technologies that have been developed for searching using inverted indices (e.g., internet search engines). And second, the query can be optimized by shifting some portions of the constraint solving down to the inverted index and its metadata. This structure may be hidden from typical end users, and the particular distribution of constraint solving can be modified and optimized over time. In contrast, in a conventional two-stage system (in which a user first searches for relevant patient records using one query and then computes valid patients using a different language), this type of modification and optimization is not possible.

The method 200 illustrated in FIG. 2 can be modified in many different ways. For example, some or all of the steps of the method 200 can be repeated. In some embodiments, the health system provides a dynamic stream or feed of patient records to the health data platform, which may include records for new patients as well as updated records for existing patients. Accordingly, the method 200 can be repeated (e.g., continuously, at predetermined intervals, when new data is available) to process the additional records. Optionally, one or more of the steps of the method 200 can be omitted (e.g., the suppression process of block 208) and/or the method 200 can include additional steps not shown in FIG. 2. As another example, method 200 may be modified to include one or more additional blocks, such as one or more blocks for automatically generating and transmitting messages to one or more users, such as a health care professional or patient. For example, in response to the health data platform receiving or acquiring new and/or updated records, the health data platform can process the new and/or updated records, automatically generate a message containing the new and/or updated records whenever new and/or updated records are received or stored, and transmit the automatically generated message to one or more users over a network in real time, so that those users have immediate access to the new and/or updated patient records, including de-identified records.

III. Methods for Searching Health Data

As discussed previously, searching health data such as patient records can be cumbersome and inefficient, particularly with very large corpuses of data (e.g., tens of millions of documents). While conventional search approaches involved multiple discrete processes directed by a user (e.g., a first query to identify a set of potential matches, and a second query that evaluates the potential matches against one or more constraints), embodiments of the present technology enable a user to submit a single query that specifies both events and temporal relationships between events. In operation, this query can be decomposed to construct an index query and a set of constraints. The index query can be executed against an inverted index to return candidate patient records. These candidate patient records can then be evaluated to solve for the constraints and return matching patient records.

Figure 3:
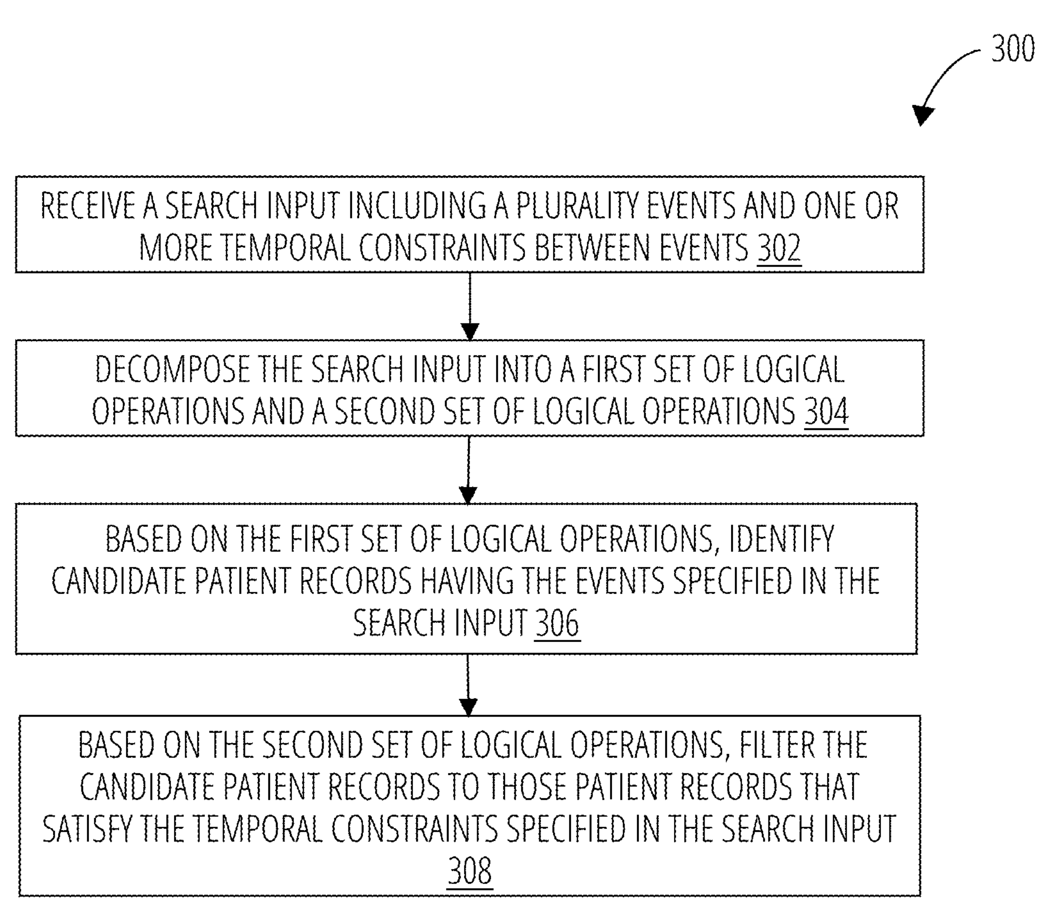
FIG. 3 illustrates an example routine for searching patient records in accordance with embodiments of the present technology.

FIG. 3 illustrates an example routine 300 for searching health data. In block 302, routine 300 receives a search input including a plurality of events and one or more specified temporal relationships between events. As described above, the events can include medical events such as diagnoses, medications, doctor visits, surgical procedures, etc., and optionally may also include patient attributes such as age, sex, gender, ethnicity, etc. The temporal relationships can specify how two or more events relate to each other in time (e.g., event A occurs before event B, event A occurs simultaneously with event B, the time interval between events A and B is greater than or equal to a certain value, the time interval between events A and B is less than a certain value, etc). For example, a user may enter a search for all patient records that include (1) diagnosis D, (2) medication M taken within 6 months of lab test L with result R. The events would be diagnosis D, medication M, lab test L, and result R; and the temporal constraints would be that medication L must be taken within 6 months of lab test L.

In block 304, routine 300 decomposes the search input into a first set of logical operations and a second set of logical operations. The first set of logical operations can represent an index query that, when applied to the search index, returns all patient records that could potentially satisfy the search request (e.g., 100% recall, but may be less than 100% precision). In some embodiments, the first set of logical operations includes evaluating whether a record includes certain index terms. These index terms can then be used to query an inverted index as discussed previously. The index terms can correspond to events on a patient timeline (e.g., diagnoses, lab results, medication administrations, doctor visits, etc.).

In block 306, the routine 300 identifies, based on the first set of logical operations, candidate patient records having the events specified in the search input. This can involve, for example, constructing an index query based on the events in the search input, which as noted above may be used to generate terms for the index query. This index query may be applied against an inverted index to return the candidate patient records.

The index terms used in the index query can be events that must be present in a patient record in order for it to be possible for the record to satisfy the search input. For example, if the user is searching for patient records that include a diagnosis D occurring before medication M is administered, the only records that could potentially satisfy the search input are records that include both diagnosis D and medication M in the patient timeline. As another example, if the user is searching for patient records that include a diagnosis D occurring before either lab test L1 or lab test L2, then the returned records must include diagnosis D, and at least one of lab test L1 or lab test L2. In some embodiments, the first set of logical operations are determined from the search input by identifying the predicate events in the search input.

In block 308, routine 300 filters, based on the second set of logical operations, the candidate patient records to those patient records that satisfy the temporal constraints specified in the search input. For example, the second set of logical operations can represent one or more constraints that filter the candidate records produced by the first set of logical operations to return only the patient records that match satisfy the search input (e.g., 100% precision). The second set of logical operations can include evaluating relationships between the particular index terms, optionally including any temporal constraints. For example, the second set of logical operations can take the form of logical expressions that combine index terms via Boolean operators (e.g., a patient record with diagnosis D AND medication M). Additionally or alternatively, the second set of logical operations can include temporal constraints (e.g., a patient record with medication M before diagnosis D). The second set of logical operations can also include inclusion and/or exclusion criteria (e.g., if the patient record includes diagnosis D it should be excluded from the final result). For example, if the search input was "all records including diagnosis D occurring before medication M," the first set of logical operations would return all records including diagnosis D and medication M, and the second set of logical operations would filter those results to return only records that include diagnosis D before medication M.

As described in more detail below, these operators can include variety of different constructs, such as resolve and compound operations, as well as inclusion and exclusion criteria.

A. Example Query Language Elements

Various examples of query language are described below. These terms, structures, and operators are described for purposes of illustration only, and the present technology need not be implemented in the manner described below. In various embodiments, some or all of the aspects of the query language can be modified to suit the particular application, as will be appreciated by one of ordinary skill in the art.

In some embodiments, a query language can include four primary components: predicate, resolve, compound, and inclusion/exclusion. A predicate can provide a Boolean operation designed for selecting events of interest. For example, a predicate may specify a diagnosis of condition X or a medication with ingredient Y administered in pill form. Predicates may be considered in the context of a single event (e.g., an event either matches the predicate or doesn't). Resolve can provide a Boolean operation designed to test for relationships between events. For example, resolve can be used to test whether a patient has a diagnosis of X followed by administration of medication Y while being aged over 60. Resolves can be considered in the context of groups of events (e.g., either a certain combination of specific events can be found to match the constraints (resolves as true), or they cannot (resolves as false)).

Compound, like resolve, operates on groups of events. Also like resolve, compound attempts to determine whether a specific list of temporal or value constraints can be satisfied (e.g., if a certain set of conditions exist on a patient record). However, rather than the output being a simple true or false, the output of a compound operation can be a new set of events. Each new even can represent an instance in which the specified conditions can be satisfied. Effectively, a compound operation combines one or more existing events into a new event representing a particular circumstance of interest. This can allow further evaluation stages (e.g., either compound or resolve operations) to treat those circumstances (potentially a complex combination of events and constraints) as a single simple event in time.

Inclusion and exclusion operators can be user-defined Boolean expressions that are used to determine whether a patient should be returned as a result of the query. Both inclusion and exclusion operators take the output of resolve operations as an input and return either true or false. For example, a patient is included in the return set only if the inclusion operation evaluates as true and the exclusion operation evaluates as false. In some examples, inclusion can be defined as "A OR (B AND C)" where A, B, C are the result of resolve operations.

The above order of these query building blocks can follow the general flow of the query execution in some examples. First, predicates may select which events from the patient's timeline are of interest to the query. Second, compound operations group those source events into more complex logical ones representing situations of interest to the user. Third, resolve operations determine whether the resulting events (both predicates and compounds) meet certain constraints. Fourth, the inclusion/exclusion operations test whether the resolved state satisfies the criteria for including a patient in a result set.

In some instances, a simple query need not use all these operations. For example, a minimum set may be a combination of one or more predicates, a single resolve, and an inclusion test.

While several examples of query language elements and operations are provided below, in various implementations the particular construction of the query language and/or the logical operators can take any suitable form. For instance, inclusion and exclusion criteria can be defined in terms of event sets and counts of events. The provided examples are intended to be non-limiting, and describe only particular suitable implementations of the present technology. As will be appreciated by one of ordinary skill in the art, the present technology can be implemented using a wide variety of query languages, particular logical operators, inclusion and exclusion criteria, etc.

i. Predicate

A predicate can be specified via the following parameters: Name (allowing the predicate to be referenced from elsewhere in the query), Type (specifying the event type the predicate operates on), and Root of a Boolean Expression Tree (a combination of AND OR operations, with associated clauses). For example, a predicate might be constructed to select the events for the medications warfarin, apixaban or rivaroxaban. In another example, a predicate may match a particular type of risk assessment provided that the value of the event property is either less than 3 or greater than 6. Additionally, a predicate can include temporal aspects, such as selecting blood thinner medication administration only after the start of 2020, or a particular diagnosis only in the month of June 2019.

ii. Filter

A filter can be applied to an input set to create a subset of the input the set. In some cases, the subset may be named. In some embodiments, each patient represented in a set of patient records may include a list of one or more predefined data sets, such as one data set for each event type, such as birth, diagnoses, lab results, vitals, medication requests, medications administered, procedures, encounters, vaccinations, observations, risk assessments, etc. Moreover, one or more of these sets may be associated with an ontology or organizational structure and set of corresponding codes or nomenclature, such as:

- ICD-10-CM: The International Classification of Diseases and Related Health Problems (ICD) Clinical Modification is used by U.S. physicians and other healthcare providers to classify and code all diagnoses, symptoms, and problems. Like its predecessor ICD-9-CM, ICD-10-CM is published by the National Center for Health Statistics of the U.S. government.
- ICD-10-PCS. The International Classification of Diseases and Related Health Problems (ICD) Procedure Coding System is used for classifying procedures performed in hospital inpatient health care settings.
- HCPCS. The Healthcare Common Procedure Coding System represents medical procedures, supplies, products, and services.
- LOINC: Logical Observation Identifiers Names and Codes was created specifically to standardize the identification and reporting of medical laboratory observations, including measurements. It has been expanded to standardize clinical observations as well.
- SNOMED CT: The Systematized Nomenclature of Medicine Clinical Terms (US Edition) is used to standardize clinical findings, disorders, body structures, procedures, microorganisms, allergies, and various other clinical domains.

NDC. The National Drug Code provides a list of all drugs manufactured or processed for off-the-shelf, commercial distribution.

CVX. The Vaccine Administered (CVX) standard covers active and inactive vaccine terms for the US.

RxNorm provides standard names for clinical drugs (active ingredient+strength) and for dose forms.

A filter can be applied to any one of the sets (or a union of the sets) as an input set to identify a corresponding subset, such as a set of all diagnoses with a corresponding ontological code (e.g., "T.1201278"), all diagnoses selected from a group of ontological codes, all diagnoses that are the child of a particular ontological code, all diagnoses that are descended from or more particular ontological codes, all risk assessments that resulted in an assessment of risk below or above a particular threshold, all events that occurred before or after a particular date/time, and so on. Moreover, filters can be applied to subsets generated by other filters.

iii. Resolve

The resolve operation is a mechanism for determining whether a specific arrangement of events exist on a patient timeline. For example, the events of interest may include a specific diagnosis, medication, and laboratory result. The search input may specify that these events need to be present on the timeline in that particular order and the gap between the first and the last cannot be greater than eight weeks. The resolve will evaluate to true if any set of three events can be found that fit that criteria for a patient.

A resolve is built from the following components: (1) one or more inputs (each defining a set of events of a single type, filtered via a predicate), (2) zero or more constraint clauses (each specifying a temporal-based or value-based constraint that the event instances must satisfy; only if all constraint clauses evaluate as true for a single set of instances will the resolve be true), and (3) an output name (e.g., the label used to reference the result of the resolve in an inclusion or exclusion expression.

An input defines a subset of events matching a specified criteria. For example, the input can define all the occasions a patient received a particular diagnosis or all the events recording a change in their personal details. An input can include, for example, a predicate (defining a filter to match events of interest) and/or an instance name (e.g., a label for the events in this input, similar to a variable name).

The clause section defines the set of constraints that must be met by the input events. For example, the clause may specify that events must be ordered a certain way or the gap between them is less than a certain amount of time. For a resolve to evaluate as true, each of its clauses must evaluate as true. Each clause can be one of a pre-defined list of constraint operations. The input parameters to the clauses are the instance labels from the input definitions. The number of input parameters and how they are interpreted can depend on the type of constraint.

Examples of temporal constraint operators include: order (e.g., constrains a list of events to match a given order), gap (e.g., constrains two events so one is either within or outside a specified time gap relative to the other), closest previous (e.g., constraints two events so that one must be the closest previous event from that input set to the other), or other such constraint operators. In various examples, other suitable temporal constraint operators can be employed, and can take any form in which the relative times between events, the time of an event relative to the patient timeline, or the time of an event relative to absolute time are evaluated.

Figure 4:
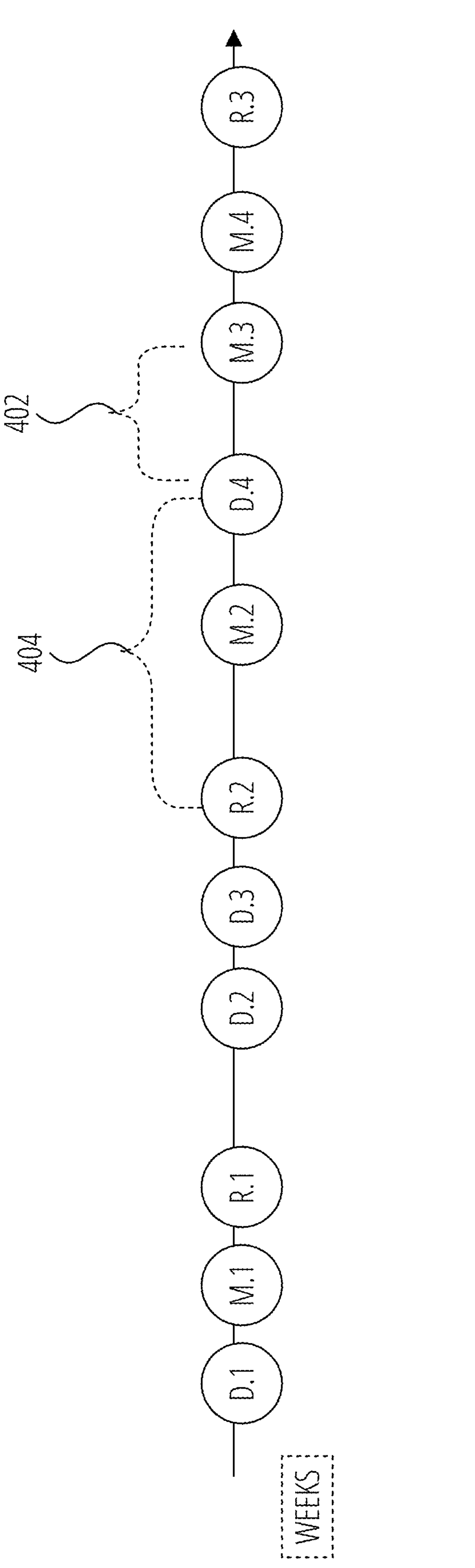
FIG. 4 illustrates an example patient timeline in accordance with embodiments of the present technology.

FIG. 4 shows an example patient timeline for purposes of illustrating a resolve operation. Consider a resolve with 3 inputs: (1) a certain diagnosis D (instance labeled D.4), (2) a given medication M (instance labeled M.3), and (3) a particular risk assessment R (instance labeled R.2). The clauses given for the resolve in this example include "Gap: D.4, M.3 less than 2 weeks" and "ClosestPrev: D.4, R.2."

In the illustrated example, there are four diagnosis events on the patient timeline. D.1 may include a medication event (M.1) within the required time gap, but there is no previous risk assessment (R.x), so the ClosestPrev clause cannot find a matching instance. Diagnosis events D.2 and D.3 do have risk assessments that satisfy the ClosetPrev clause (R.1), however, they do not have a medication event within the required gap (i.e., M.2 is more than 2 weeks beyond D.2 and D.3). Finally, the fourth diagnosis event, D.4, has both a medication event within range (indicated by range 402) and a previous risk assessment that satisfies the ClosestPrev clause (indicated by range 404). As such, the diagnosis event D.4, medication event M.2, and risk assessment event R.2 satisfy the resolve operator, which provides an output of true.

If, in this example, the ClosestPrev clause had been omitted, then the combination of (D.1, M.1, R.1) would also have satisfied the resolve, since there would be no explicit ordering between the risk assessment and the diagnosis. If an order clause were added, then (D.4, M.3, R.1) would have also satisfied the resolve. Only with ClosestPrev can the query ensure that the risk assessment is both before and closest to the diagnosis.

Note that it may be possible to build more complex constraints by combining multiple instances of clauses together. For example, consider a case in which four events (a, b, c, d) are provided and the query is intended to constrain "a" to be first, "d" to be last, but the order of "b" and "c" is irrelevant. As a result, ordering [a, b, c, d] and [a, c, b, d] should both resolve as valid. This can be achieved by the following set of order clauses: (1) Order—["a", "b", "d" ], and (2) Order—["a", "c", "d"]. This ensures the relative ordering of both "b" and "c" with respect to "a" and "d", but implies nothing about the relative ordering of "b" and "c" with respect to each other.

Additional examples of constrain clauses include: ClosestNext (identifying the nearest subsequent event), Satisfies (e.g., evaluates to true only if the event instance satisfies the predicate), FirstN (e.g., taking an event instance and a count n, evaluating to true if the event instance is within the first n from its input set), LastN (e.g., similar to FirstN but working backwards from the end of the input set), and Within (e.g., taking two or more event instances and a time span, evaluating to true if all event instances fall within the time span, regardless of order). In some embodiments, one or more inputs may not be referenced in any clauses. If such an input is defined but not constrained, then any event from that input will satisfy the resolve operation. As such, the simplest possible resolve operation has zero clauses. In that case the resolve will be true so long as there is at least one event instance found for each of its inputs.

The output of a resolve can be defined by a label. That label can then be referenced as part of the inclusion and exclusions criteria.

iv. Compound

The compound operation can be similar to the resolve operation in many ways. For example, compound can take the same input parameters and use the same set of clauses described above with respect to the resolve operation. Compound can therefore perform the same evaluations of constraints between events. The compound operation can differ, however, in its output. While a resolve operation outputs a Boolean value and stops evaluation on the first valid input event set, a compound operation can output events and continue its evaluation until all valid input sets have been discovered.

Figure 5A:
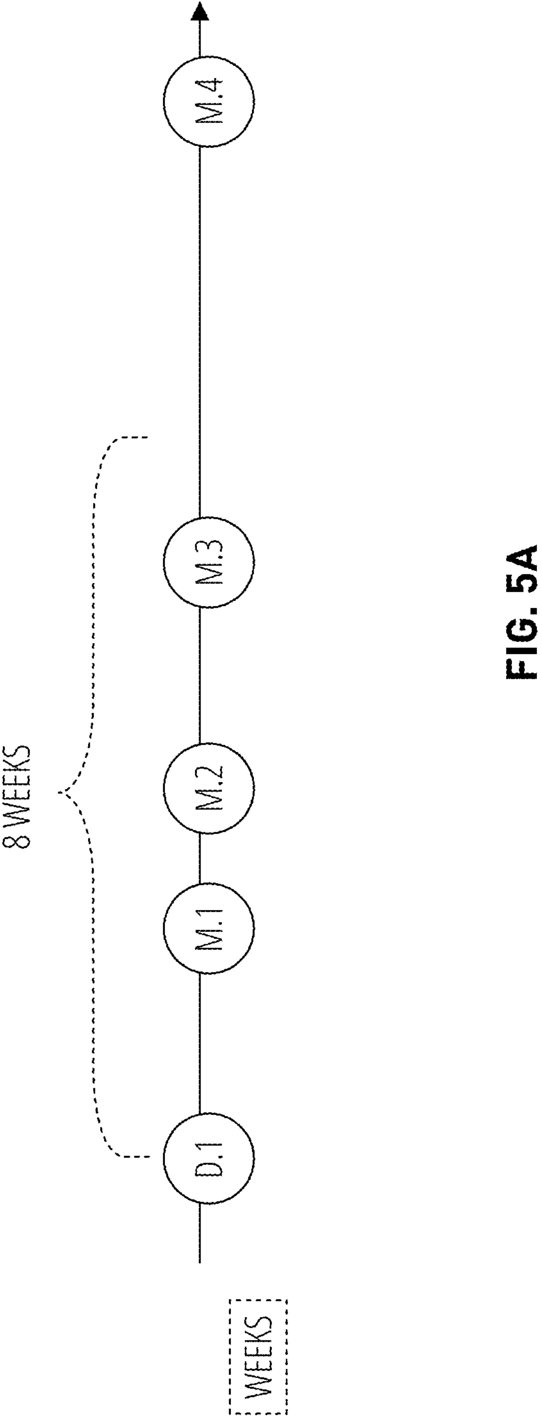
FIG. 5A illustrates an example patient timeline in accordance with embodiments of the present technology.

Consider, for example, a patient timeline as shown in FIG. 5A, with a diagnosis event D.1 and four medication events M.1, M.2, M.3, and M.4. An example compound operation can include two inputs: a diagnosis of type D and medication of type M. The compound operation can also include the constraint that a medication event M exists 8 weeks or less after the diagnosis D.

In the timeline illustrated in FIG. 5A, there are three pairs that satisfy the constraint: (D.1-M.1), (D.1-M.2), and (D.1-M.3). In this case, the compound operation identifies all three pairs and outputs a compound event for each unique pair. If the same evaluation were run in a resolve operation, it would early out with a TRUE output upon detecting the first pair (D.1-M.1).

Figure 5B:
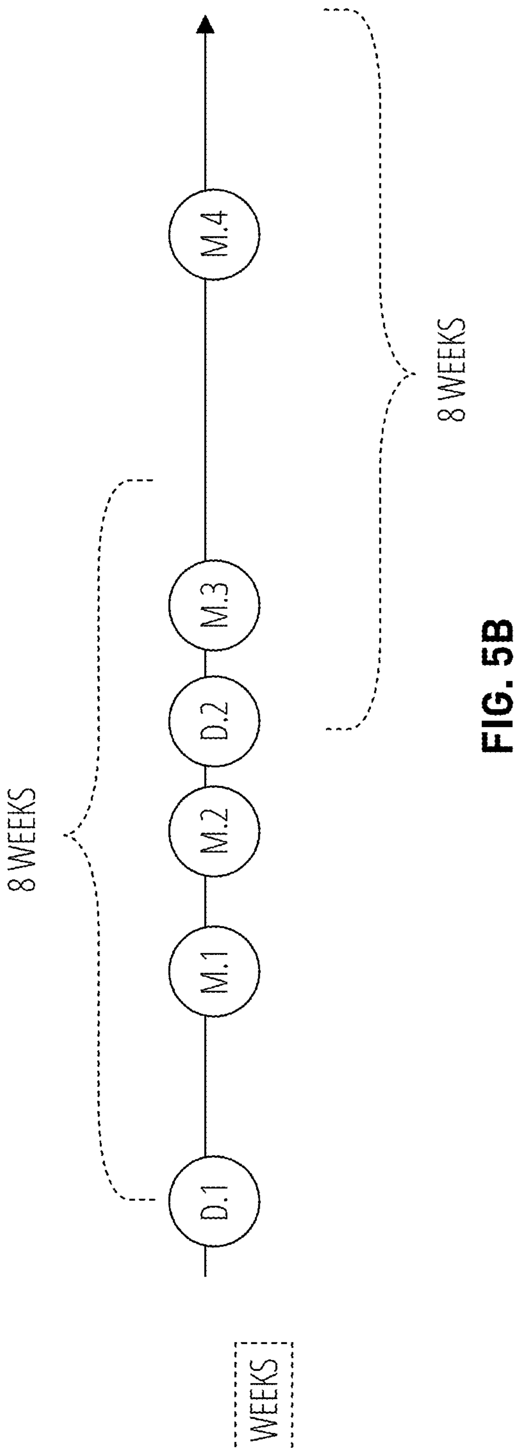
FIG. 5B illustrates an example patient timeline in accordance with embodiments of the present technology.

If new diagnosis event—D.2—were introduced into the timeline as shown in FIG. 5B, then there are 5 unique event instances: (D.1-M.1), (D.1-M.2), (D.1-M.3), (D.2-M.3) and (D.2-M.4). The compound operation would therefore output 5 new events.

In some examples, the number of combinations found can be reduced by adding more constraints. For example, adding a 'FirstN where N=1' constraint to the diagnosis D event would prevent D.2 being considered for evaluation. Adding a ClosestNext constraint between D and M would prevent pairs (D.1-M.2), (D.1-M.3) and (D.2-M.4) being considered. And adding both constraints (First "D" and ClosestNext "M" to "D") would result in (D.1-M.1) being left as the only valid pair on the timeline shown in FIG. 5B.

In some embodiments, the events created by a compound operation may be temporary and be retained in memory only for the length of time that it takes the query to run on a patient timeline. For example, such output events may not persist in the patient record or between queries. Alternatively, the outputs of compound operations can persist in the patient record(s) in at least some embodiments.

The output of a compound operation can be defined with two parameters. These include (1) Type (e.g., a user-defined string) and (2) Timestamp (e.g., a timestamp for the event, such as one of the timestamps from the input event set). In some examples, multiple compound operations can be combined to output the same event type. For example, consider the case in which there are a number of different pre-conditions that to be evaluated. For the patient to be selected, at least one of these different pre-conditions must exist prior to the index event. However, since the particular set of circumstances that led to the pre-condition are not relevant (only that there is at least one instance), the query can contain multiple compound operations, each defining the constraints for a different pre-condition, but all outputting a common "PreCond" event type. The resolve operator(s) can receive as an input this single "PreCond" type without regard to which particular cases the patient had. In this case the query execution engine can run all the compounding operations for the same event type before running any downstream components that receive it as an input. The input to downstream resolve operators and other processes can therefore be a union of the outputs from upstream.

Compound events can serve as the underlying mechanism for handling an index event concept. For example, a compound operation can create a specific shared event type, which can then be accessed by multiple resolve operations, which in turn can be used in both inclusion and exclusion expressions. In fact, compound events can represent a generalization of the index event concept. Rather than a single special event, there may be N of them. If the query wishes to just use a single denoted index type, or even a single instance of that type, then the query may be limited in that manner.

v. Sequence

A sequence operation takes one or more input event sets and produces an output event set, one new event for all unique event sequences it can find that match the given constraints. For example, one sequence would be detecting two covid vaccinations events greater than 2 weeks apart, represented as the following:

```
VaccinatedEvents = sequence ( CovidVaccineEvents a,
CovidVaccineEvents b)
{
  b.Timestamp - a.Timestamp > 2wk
}
```

In this example, this syntax corresponds to finding a single event "a" from a set of events labelled "CovidVaccineEvents" and a single event "b" from the same set. For each identified unique pair (a, b) that are greater than 2 weeks apart, the system creates new event in a set of events labelled "VaccinatedEvents." For example, if the CovidVaccineEvents set contains 3 events A, B and C, with 1 month between each of them, there will be 3 output events generated from pairs (A,B) (A, C) (B, C). In some cases, the system may apply a user-generated control on the maximum number of events that can be output.

In some embodiments, each sequence operation includes a Boolean expression that specifies conditions under which an output event may be created. For each unique combination of input events that satisfy the expression, a single output event is generated. The expression is essentially a series of constraints between the different properties of the input events, such as a.TimeStamp<b.TimeStamp AND b.TimeStamp<c. TimeStamp to specify that three events (a, b, and c) must have occurred in a particular order. In addition to comparison operations, the system may employ additional operations, such as:

- Gap(a,b)—Returns the time interval between a and b.
- Order(a, b, c, d, . . . )—Returns true if events are ordered in time as listed
- Associated(a,b)—Returns true if event a and b are from the same encounter (i.e. associated by an encounter id)
- Count(EventSet, a, b)—Returns the count of events in 'EventSet' between time of 'a' and 'b'
- ClosestPrev/Next(a,b)—Returns true if 'a' is the closest previous or next event to b
- Average(a.NumericValue, b.NumericValue, c.NumericValue, . . . )—Returns the average of N values.

One of ordinary skill in the art will recognize that any number of operations may be applied or employed to use sequences to generate events.

vi. Inclusion and Exclusion

In the final stage of query evaluation, inclusion and/or exclusion operators can be applied. Each can take the form of a Boolean expression tree that takes the results of resolve operations and determines whether a particular patient should be included or excluded. For example, if upstream resolve outputs are Ra, Rb, Rc, and Rd, then these may be combined via inclusion and/or exclusion operators such as Ra AND Rb AND (Rc OR Rd). Having evaluated both the inclusion and exclusion expressions the patient is only returned in the query results if "Inclusion AND NOT Exclusion" evaluates as TRUE. For example, a researcher may wish to include all patients with more than two MMR vaccinations but exclude those patients under the age of 30.

In some examples, a typical inclusion expression can take the form—(Ra AND Rb AND Rc AND Rd AND . . . ). Similarly, a typical exclusion expression can take the form—(Ru OR Ry OR Rx OR Rz OR . . . ) Accordingly, the general criteria (combining the inclusion and exclusion criteria into a single expression) may take the form of—Ra AND Rb AND Rc AND NOT (Rx OR Ry OR Rz). However, this formulation is only one example, and in various embodiments inclusion and exclusion can be specified as any suitable mixture of AND/OR operations, thereby imparting flexibility for more complex query formulation. In some embodiments, there is, at a minimum, one inclusion expression provided with at least one input in its tree. The exclusion expression may be optional.

vii. Returning Data

A query can return the patient identities and/or patient records that are matched at least by the inclusion/exclusion criteria. In some examples, the query can also return the details of the specific events that the query matched. Alternatively, a "return" operation can define which resolve operations have data returned from their input event set. For example, consider the formulation: Inclusion=Ra AND Rb AND Rc Return=Rb, Rc. In this case, if a patient matches the query, then resolves "a", "b" and "c" must have been true. The return operator then specifies that the matching input events just from resolve "b" and "c" should be passed back with the patient identity.

In some cases, depending on the formulation of the inclusion set, it may only be possible to satisfy a subset of the return request. For example, consider this formulation: Inclusion=Ra AND (Rb OR Rc) Return=Ra, Rc. In this case Ra would always be returned, but Rc may or may not. If Rb evaluated as TRUE then Rc likely would not have been executed at all. Optionally, the caller can choose to formulate a resolve specifically for returning data and add it to the inclusion expression via an AND operator. For example, the caller could reformulate the above as: Inclusion=Ra AND (Rb OR Rc) AND Rd Return=Rd, in which Rd has been created to pick out the event data the caller requires from the patient timeline.

One of ordinary skill in the art will recognize that various logical operators, inclusion and exclusion criteria, etc. can be combined in any number of ways to produce search results. For example, in one embodiment the disclosed system uses predicates to filter events and compounds and/or resolves to look for patterns in the filtered events. As discussed above, a resolve operation outputs a Boolean value and stops evaluation on the first valid input event set while a compound operation can output events and continue its evaluation until all valid input sets have been discovered. Finally, the disclosed system may apply inclusion/exclusion criteria to determine whether a patient matches based on the set of events associated with the patient and the inclusion/exclusion criteria.

In another embodiment, the disclosed system uses filter operations to filter one or more sets of events and then optionally uses union operations to merge sets of events into a single set of events. Furthermore, the system can use sequence operations to identify specific patterns of events in sets of events, each identified pattern corresponding to a new event in a resulting output set of events. Finally, the disclosed system may apply inclusion/exclusion criteria to determine whether a patient matches based on the set of events associated with the patient and the inclusion/exclusion criteria.

B. Example Query Construction and Execution

As noted above, a user-defined search query can be decomposed and used to construct an index query based on predicates, compound and resolve operators, and inclusion/exclusion criteria. In various examples, some or all of these elements can include temporal aspects (e.g., temporal relationships between events, or temporal relationships between an event and absolute time, patient age, or otherwise). Additional details regarding constructing and executing an index query to be applied against an inverted index are provided below. As noted previously, these examples are illustrative only, and various aspects of the processes described herein may be modified, re-arranged, substituted, omitted, or expanded upon as deemed suitable for a given application.

In some embodiments, query execution can include two primary steps. First, an index query is constructed to apply against an inverted index. And second, the matching patient records can be evaluated against the specified constraints. The first step may be performed just once per query, while the second step may be performed for each query and patient record pair.

i. Constructing the Index Query

After a user search input is received, the predicates within the query can be optimized. This can include, for example, flattening any unnecessary layers in the expression and combining clauses into the fewest possible number of nodes.

Next, index terms can be generated from predicate clauses. When a patient record is indexed, the index terms derived from its events are stored (e.g., in a posting list as described previously). As one example, for a diagnosis of atrial fibrillation, the term "ev_diagnosis_diagnosis_t.528550" can be stored. This term can be read as: this patient has an event of type diagnosis with a property called diagnosis with a value of T.528550. This same approach can be taken on the query side using predicates from the search input. If a search predicate includes "Diagnosis contains T.528550," then the query will only match events with a diagnosis property of T. 528550. The query should therefore fetch all the patient records with those events on their timelines. This clause may be written into the index search term as, for example, "ev_diagnosis_diagnosis_t. 528550"

Next, the index terms can be combined into predicate search trees. The individual clauses in a predicate can be part of a Boolean expression tree that also needs to be built into the search query. For example, a predicate clause can be used that returns values that match any one of three medications. Once the individual predicate clauses are turned into index terms, they can be combined together into the search query using the Boolean operations from the predicate. For example, a predicate identifying three different medications connected via an OR operation can be transformed into this mini-search query: {ev_medicationexposure_medication_t.880495 OR ev_medicationexposure_medication_t.883342 OR ev_medicationexposure_medication_t.924402}. This query will match patients who have had any one of the three specified medications administered.

The predicate search trees may then be combined into resolve/compound search trees via an AND operator. As noted previously, each input into a resolve operation is associated with a predicate. For a resolve to be satisfied, each of its inputs must be satisfied. The predicate search trees can therefore be combined using an AND relationship based on the resolves that they are in. For example, consider a resolve operation that takes input predicates AFibDiagnosis and BloodThinnerPredicate and evaluates them for a gap of less than four weeks. Furthermore, the input predicate BloodThinnerPredicate can return as true if any one of three specified medications were administered. Accordingly, the resolve operation resolves as true if it can find an AFibDiagnosis with a nearby medication event using one of three possible anticoagulants.

As noted above, the predicates can be turned into the following predicate search trees: (1) {ev_diagnosis_diagnosis_t.528550}; and (2) {ev_medicationexposure_medication_t.880495 OR ev_medicationexposure_medication_t.883342 OR ev_medicationexposure_medication_t.924402}. For the resolve to be satisfied, it must find events for both these inputs. Accordingly, these can be further combined into the search query:

```
{ev__diagnosis__diagnosis__t.528550 AND
(ev__medicationexposure__medication__t.880495 OR
ev__medicationexposure__medication__t.883342 OR
ev__medicationexposure__medication__t.924402
)}.
```

In operation, this query will return patients who have been diagnosed with AFibDiagnosis and given at least one of the three specified anticoagulants.

Next, the compound search trees that output the same event type can be combined via an OR operator. For example, there may be multiple compound operations detecting different ways to be diagnosed with diabetes, but downstream resolve operations only require a single type of diabetes event. As such, the search trees can be combined together with an OR operation, so as to find all patient records in the index that can create the compound event in any one of the different possible ways.

The resolve/compound search trees may then be combined using an inclusion expression tree. In some examples, this is the final step before issuing the query to the inverted index. For example, consider case of three resolves—Ra, Rb, Rc—combined together for inclusion as—Ra AND (Rb OR Rc). In this case, the query can be constructed by merging the three index trees from each resolve using the same AND/OR combination. This will then return patient records from the inverted index that have the necessary events to satisfy the inputs of Ra and either the necessary events for Rb or the necessary events for Rc.

The final search query can therefore take the form of a complex multi-clause query. Predicate trees can be combined into compound trees, which can then be combined into resolve trees, which finally can be combined via an inclusion tree. While this approach outlined does not include exclusion criteria within the initial search, in various embodiments exclusion criteria can be included, similar to the inclusion criteria above (e.g., constructing exclusion trees). Alternatively, exclusion criteria can be applied after search results are obtained via the inclusion trees.

Additionally, although the process here is described as beginning with the predicates and working towards the inclusion operation, in various implementations the process may instead begin with inclusion criteria and use a directed acyclic graph (DAG) to work backwards, only building what is needed to execute the query. For example, if a resolve clause is used only in the exclusion expression, then there's no need to build a search tree for it for an inclusion tree.

Figure 6:
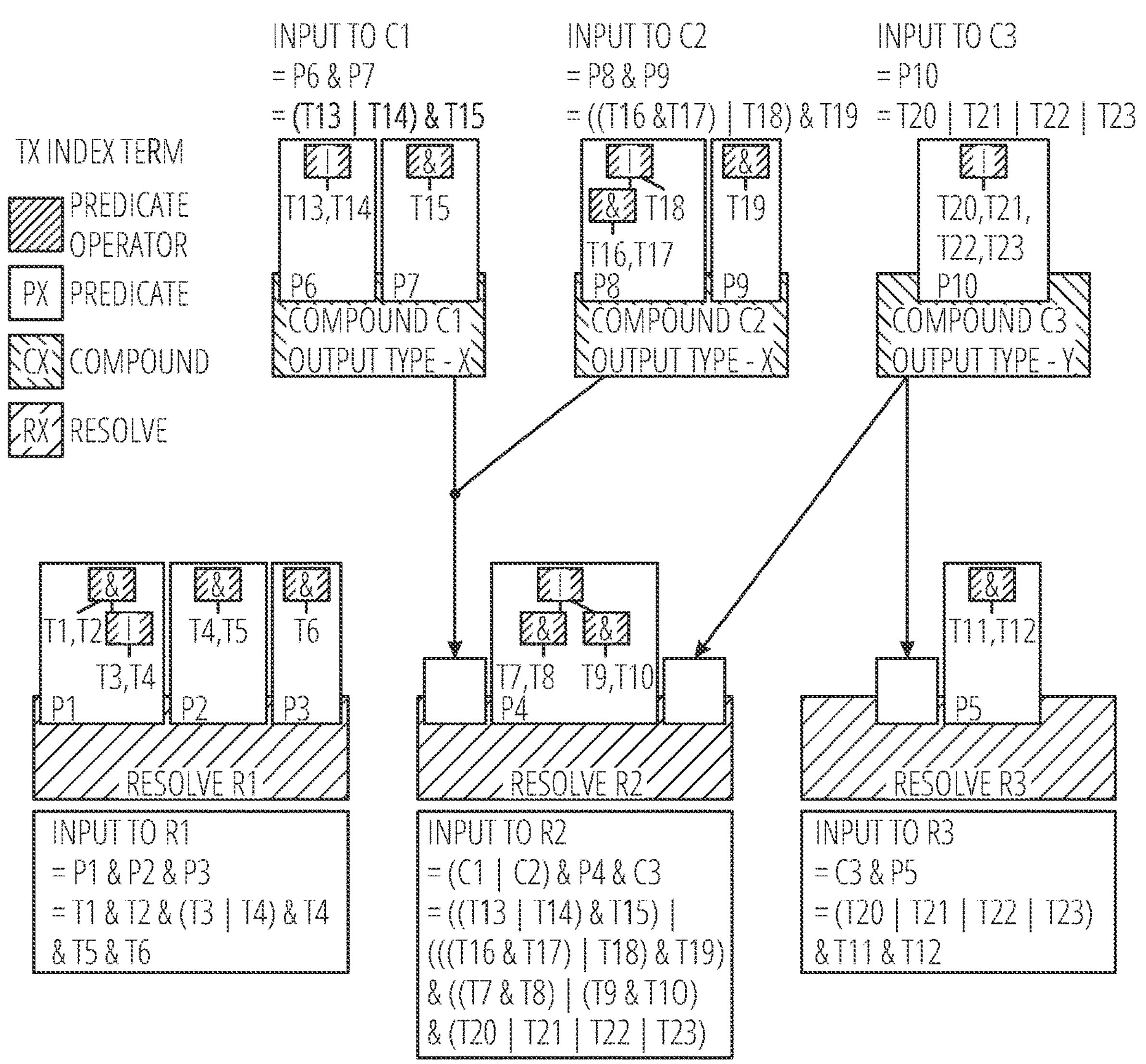
FIG. 6 illustrates a schematic diagram of an example query construction in accordance with embodiments of the present technology.

FIG. 6 is a diagram illustrating an example of constructing a multi-clause query by combining various search trees. As illustrated, the final index query, expressed as a sequence of search terms and AND/OR operations, can be built from the query structure.

- Predicate clauses are turned into terms to find in the inverted index (e.g., t1, t2, t3, t4, etc.).
- The predicate expression trees (P1-P10) groups the terms together into mini-search queries (e.g., a query to return patients with a possibility of satisfying the predicate).
- The compound operators (C1-C3) aggregate predicate search queries together into larger search queries (e.g., a query to return patients capable of satisfying the compound operation and outputting an event from it).
- The resolve operators (R1-R3) group both predicate and compound operator queries together (e.g., a query returning patients that could both match the predicates for the resolve and generate the upstream compound events needed).
- The inclusion criteria groups the resolve queries together to form the final query issued (e.g., a query capable of finding patients who could meet the resolves necessary to satisfy the inclusion criteria).

i. Executing the Index Query and Evaluating Matching Records

Once the index query has been constructed as outlined above, it can be executed against the inverted index to retrieve all matching patient records. In some examples, this can be an iterative process, in which patient records are evaluated and fetched in parallel. For example, in the scenario illustrated in FIG. 6, the index query can be executed against an inverted index to return all patient records. As noted previously, this process may return all patient records that could match, but will likely also return at least some patient records that do not satisfy all the constraints (e.g., inclusion and exclusion criteria). In other words, the index query may have 100% recall but less than 100% precision.

Optionally, the patient records may deserialized or otherwise modified to account for any time-shifting performed during upstream processing. In some instances, individual patient records may be modified to preserve anonymity, including by shifting or otherwise modifying time values. In such instances, a post-retrieval processing step can perform corrective time shifting or other modifications to account for the upstream processing steps.

Next, the inclusion and exclusion expressions can be evaluated. The specific order of these processes can vary based on optimization decisions. For example, if inclusion is being tested first, but the query is finding that 99% of patient records are passing that but failing the exclusion test, it would be more efficient to first test for the exclusion expressions.

As the query evaluation walks up the inclusion/exclusion expression trees, the resolve, compound, and/or sequence operations that are needed for the inclusion and/or exclusion expressions are evaluated. For example, the inclusion/exclusion expression trees may require the output of resolve operations, which in turn may require the output of compound operations. Both the resolve and compound operations will in turn also require event sets filtered via predicates.

Accordingly, this evaluation can take the form of a tree walk, such as a lazy evaluation over a dependency tree. The resolve operations in the inclusion/exclusion expressions are the leaves of the tree, and the compound operations are the internal nodes. For each node in the tree, the query filters out the required events and solves against the given constraint clauses.

For example, returning to the diagram shown in FIG. 6.

- The inclusion criteria is "R1 & R2 & R3". In this example, the resolves will be addressed in this order, though in various embodiments the optimizer may determine in what order to execute the resolves.
- R1 has 3 inputs and has no compound event dependency. To execute it, the input predicates P1, P2, and P3 are used to filter the events from the patient timeline and the constraints resolved.
- If R1 evaluates as false than query execution for this patient can terminate early.
- R2 has 3 inputs, 2 of them being compound event types. So, before evaluation, the compound events C1, C2, and C3 must be created.
- One input depends on event type X, which is created from 2 compound operations—C1 and C2. Both C1 and C2 are therefore run to produce this event set X.
- The other input is event type Y, generated by evaluating C3.
- Once all the upstream compound operations completed, R2 can be evaluated. If it evaluates to false, then query evaluation for this patient can terminate early.
- Finally, R3 can be evaluated. This has a dependency on Compound Event Type Y. However, the preceding step already generated that set events when evaluating R2. Accordingly, R3 can be evaluated immediately, using its input predicates on the patient timeline events (P5) and the compound event type Y (C3).

Once the inclusion/exclusion expression trees have been evaluated, the matching patient records are retrieved and passed back via a "return" operation. In some embodiments, for each patient record that satisfies the inclusion/exclusion criteria, an identity can be returned. Additionally or alternatively, all events from the resolves that are specified in the return operation and that were both executed and evaluated as true can be returned.

C. Example User Interface

Figure 7:
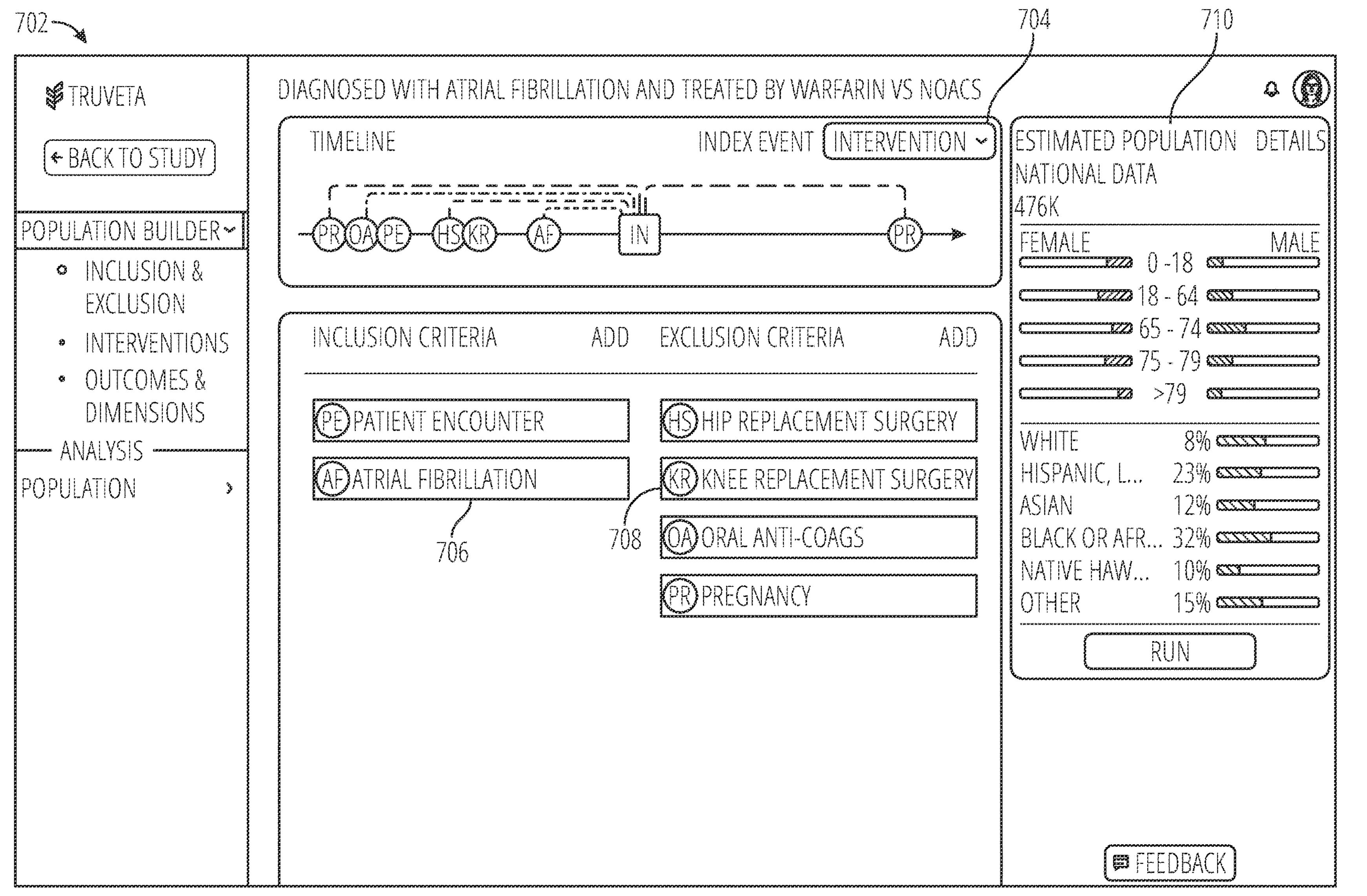
FIG. 7 illustrates an example search user interface in accordance with embodiments of the present technology.

FIG. 7 illustrates an example user interface for searching health data such as patient records. In the illustrated example, the interface 702 includes a graphical representation of a timeline 704 along with regions for designating inclusion criteria (706) and exclusion criteria (708). The temporal component of these criteria can be reflected in positioning on the timeline 704. In the illustrated example, the timeline 704 illustrates the temporal positioning of a given event relative to an index event (here an intervention). The illustrated search will return patient records in which both a patient encounter and a diagnosis of atrial fibrillation occurred before the index event, and will exclude patient records in which administration of oral anti-coagulates, knee replacement surgery, or hip replacement surgery occurred prior to the index event. Additionally, this search will exclude patient records with pregnancy, regardless of when the pregnancy event occurred relative to the timeline.

Region 710 illustrates a graphical display of an estimated population that will be returned based on the constructed query. This can include breakdowns by gender, age groups, ethnicity, or other demographic factors. The interface 702 illustrates one example of a search interface accessible to users such as clinicians and researchers, however in other embodiments the search input can be received in other ways, such as via a text-only interface or otherwise.

Examples

The following examples are included to further describe some aspects of the present technology, and should not be used to limit the scope of the technology.

Example 1. A method for querying patient records, the method comprising:

receiving a search input that specifies a plurality of events, one or more temporal relationships between the events, and inclusion and/or exclusion criteria;

constructing a search query from the search input, the search query including an index query and one or more constraints, wherein the index query is based at least in part on the plurality of events within the search input, and the one or more constraints are based at least in part on the temporal relationships and the inclusion and/or exclusion criteria from the search input;

executing the index query against an inverted index to identify matching patient records;

solving the one or more constraints against the identified matching patient records; and returning patient records that satisfy the one or more constraints.

Example 2. The method of Example 1, wherein constructing the search query further comprises generating index terms based on the plurality of events.

Example 3. The method of any one of the preceding Examples, wherein constructing the search query further comprises combining a plurality of index terms via one or more Boolean operators.

Example 4. The method of any one of the preceding Examples, wherein constructing the search query further comprises:

generating predicate clauses based at least in part on the events within the search input; and designating the predicate clauses as inputs to one or more operators, the operator(s) returning a set of events if a specified temporal relationship based on the predicate clauses is identified.

Example 5. The method of any one of the preceding Examples, wherein constructing the search query further comprises:

generating predicate clauses based at least in part on the events within the search input; and designating the predicate clauses as inputs to one or more operators, the operator(s) returning a true or false designation depending on whether a specified temporal relationship based on the predicate clauses is identified.

Example 6. The method of any one of the preceding Examples, wherein solving the one or more constraints against the identified matching patient records comprises applying the inclusion and/or exclusion criteria from the search input.

Example 7. The method of any one of the preceding Examples, wherein solving the constraints comprises determining whether each identified matching patient record includes events having the temporal relationships from the search input.

Example 8. The method of any one of the preceding Examples, wherein the events include one or more of: a diagnosis, a medication, or a lab result.

Example 9. The method of any one of the preceding Examples, wherein the inverted index is constructed from a plurality of de-identified patient records.

Example 10. The method of any one of the preceding Examples, further comprising, after building the index query, enhancing the index query using constraints from the search input, and wherein issuing the index query to the inverted index comprises using the enhanced index query.

Example 11. A method for processing a search request for patient records, the method comprising:

receiving a user input including a search input with a plurality of events with at least one specified temporal relationship;

generating index terms based on the events;

combining the index terms into predicate search trees;

combining two or more of the predicate search trees via Boolean operator(s);

generating a multi-clause query based on the combined predicate search trees; and applying the multi-clause query to a corpus of target data to obtain a plurality of matching patient records.

Example 12. The method of any one of the preceding Examples, wherein combining two or more of the predicate search trees via Boolean operators comprises combining two or more of the predicate search trees into compound trees via an AND operation.

Example 13. The method of any one of the preceding Examples, wherein combining two or more of the predicate search trees via Boolean operators comprises generating a compound tree by combining two or more of the predicate search trees that output a same event type via an OR operation.

Example 14. The method of any one of the preceding Examples, wherein a compound operation of the compound tree returns one or more events corresponding to a satisfied constraint with at least one temporal component.

Example 15. The method of any one of the preceding Examples, wherein combining two or more of the predicate search trees via Boolean operators comprises generating a compound tree by combining two or more predicate search trees with one or more compound search trees into a resolve tree.

Example 16. The method of any one of the preceding Examples, wherein a resolve operation returns a single true or false value corresponding to a satisfied or failed constraint with at least one temporal component.

Example 17. The method of any one of the preceding Examples, further comprising optimizing the predicate clauses prior to generating the index terms based on the predicate clauses.

Example 18. The method of any one of the preceding Examples, wherein optimizing the predicate clauses comprises flattening layers in the predicate clauses and/or combining predicate clauses together.

Example 19. The method of any one of the preceding Examples, wherein generating the multi-clause query further comprises applying inclusion and/or exclusion criteria to the combined predicate search tree(s).

Example 20. The method of any one of the preceding Examples, further comprising, after applying the multi-clause query to the corpus of target data to obtain the plurality of matching documents, modifying one or more of the matching documents to account for time-shifting in the target data.

Example 21. The method of any one of the preceding Examples, wherein applying the multi-clause query comprises a tree walk with a lazy evaluation.

Example 22. The method of any one of the preceding Examples, wherein the predicate clauses correspond to one or more medical events associated with a patient record.

Example 23. The method of any one of the preceding Examples, wherein the predicate clauses define the temporal constraints in terms of one or more of: a time between events, an order of events, or a time of events relative to a patient timeline.

Example 24. A method for searching patient records, the method comprising:

receiving a search input including a plurality of events and one or more temporal constraints between events;

decomposing the search input into a first set of logical operations and a second set of logical operations;

based on the first set of logical operations, identifying candidate patient records having the events specified in the search input; and based on the second set of logical operations, filtering the candidate patient records to those patient records that satisfy the temporal constraints specified in the search input.

Example 25. The method of any one of the preceding Examples, wherein the first set of logical operations comprises applying an index query against an inverted index, wherein the index query comprises index terms based on the plurality of events in the search input.

Example 26. The method of any one of the preceding Examples, wherein the second set of logical operations comprises one or more decision trees specifying logical relationships between the events.

Example 26. A method of generating an inverted index for patient records, the method comprising:

receiving, at a health data platform, a set of patient records from one or more health systems;

processing the set of patient records at the health data platform, wherein the processing includes converting the set of patient records into a common format;

generating a plurality of index terms for each patient record; and storing the index terms and corresponding matching patient records in a posting list.

Example 27. The method of any one of the preceding Examples, wherein processing the set of patient records further includes generating a set of de-identified records from the set of patient records, and wherein generating the plurality of index terms for each patient records comprises generating the plurality of index terms for each de-identified record.

Example 28. The method of any one of the preceding Examples, wherein generating the plurality of index terms comprises encoding one or more patient events.

Example 29. The method of any one of the preceding Examples, wherein encoding the one or more patient events comprises assigning an alphabetical, numerical, or alphanumerical value to the one or more patient events.

Example 30. The method of any one of the preceding Examples, wherein the one or more patient events comprises one or more of: a medical condition, a diagnosis, a test result, a medical procedure, or a medication.

Example 31. The method of any one of the preceding Examples, wherein generating the plurality of index terms comprises encoding a temporal component for the one or more events.

Example 32. The method of any one of the preceding Examples, wherein encoding the temporal component comprises assigning a value corresponding to a time relative to a patient timeline.

Example 33. A computing system comprising: one or more processors; and data storage having instructions thereon that, when executed by the one or more processors, cause the computing system to perform operations comprising the method of any one of the preceding Examples.

Example 34. One or more tangible, non-transitory computer-readable media storing instructions that, when executed by one or more processors of a computing system, cause the computing system to perform operations comprising the method of any one of the preceding Examples.

Example 35. The method of any one of the preceding Examples, further comprising:

receiving one or more of the patient records;

providing remote access to users over a network so that any one or more of the users can provide at least one updated patient record in real time through an interface, wherein at least one of the users provides an updated patient record in a format other than a common format, wherein the format other than the common format is dependent on hardware and software platform used by the at least one user;

converting the at least one updated patient record into the common format;

generating a plurality of index terms for the at least one updated patient record;

storing the index terms and corresponding matching patient records in a posting list;

generating a set of at least one de-identified record from the at least one updated patient record;

storing the converted at least one updated patient record;

after storing the converted at least one updated patient record, generating a message containing the converted at least one updated patient record; and transmitting the message to one or more users over the network in real time, so that the users have access to the updated patient record.

CONCLUSION

Although many of the embodiments are described above with respect to systems, devices, and methods for indexing and searching patient data, the technology is applicable to other applications and/or other approaches, such as indexing and/or searching other types of data (e.g., financial records, educational records, political information, location data, and/or other personal information). The approaches disclosed herein may be particularly useful for instances in which the data includes at least some temporal component. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-7.

The various processes described herein can be partially or fully implemented using program code including instructions executable by one or more processors of a computing system for implementing specific logical functions or steps in the process. The program code can be stored on any type of computer-readable medium, such as a storage device including a disk or hard drive. Computer-readable media containing code, or portions of code, can include any appropriate media known in the art, such as non-transitory computer-readable storage media. Computer-readable media can include volatile and non-volatile, removable and non-removable media implemented in any method or technology for storage and/or transmission of information, including, but not limited to, random-access memory (RAM), read-only memory (ROM), electrically erasable programmable read-only memory (EEPROM), flash memory, or other memory technology; compact disc read-only memory (CD-ROM), digital video disc (DVD), or other optical storage; magnetic cassettes, magnetic tape, magnetic disk storage, or other magnetic storage devices; solid state drives (SSD) or other solid state storage devices; or any other medium which can be used to store the desired information and which can be accessed by a system device.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded.

To the extent any materials incorporated herein by reference conflict with the present disclosure, the present disclosure controls.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A method for querying patient records, the method comprising:

receiving a search input that specifies a plurality of events and one or more temporal relationships between the events, wherein the one or more temporal relationships include a temporal relationship that specifies a first event from a first input event set, a second event from a second input event set, wherein the second input event set is different from the first input event set, and a maximum time gap between the first event and the second event, and that the first event is the closest previous event from the first input event set to the second event;

constructing a search query from the search input, the search query including an index query and one or more constraints, wherein the index query is based at least in part on the plurality of events within the search input, and the one or more constraints are based at least in part on the one or more temporal relationships from the search input;

executing the index query against an inverted index to identify matching patient records;

solving the one or more constraints against the identified matching patient records; and returning patient records that satisfy the one or more constraints.

2. The method of claim 1, further comprising:

receiving a user input including a second search input with a second plurality of events with at least one specified temporal relationship;

generating index terms based on the second plurality of events;

combining the generated index terms into predicate search trees;

combining two or more of the predicate search trees via Boolean operator(s);

generating a multi-clause query based on the combined predicate search trees; and applying the multi-clause query to a corpus of target data to obtain a plurality of matching patient records.

3. The method of claim 1, wherein receiving the search input that specifies the plurality of events and one or more temporal relationships between the events comprises receiving one or more temporal constraints between events, the method further comprising:

decomposing the search input into a first set of logical operations and a second set of logical operations;

based on the first set of logical operations, identifying candidate patient records having the events specified in the search input; and based on the second set of logical operations, filtering the candidate patient records to those patient records that satisfy the temporal constraints specified in the search input.

4. The method of claim 1, further comprising:

generating an inverted index for patient records, wherein the generating comprises:

receiving, at a health data platform, a set of patient records from one or more health systems;

processing the set of patient records at the health data platform, wherein the processing includes converting the set of patient records into a common format;

generating a plurality of index terms for each patient record; and storing the index terms and corresponding matching patient records in a posting list.

5. The method of claim 1, wherein constructing the search query further comprises generating index terms based on the plurality of events.

6. The method of claim 5, wherein constructing the search query further comprises combining a plurality of index terms via one or more Boolean operators.

7. The method of claim 1, wherein constructing the search query further comprises:

generating predicate clauses based at least in part on the events within the search input; and designating the predicate clauses as inputs to one or more operators, the operator(s) returning a set of events if a specified temporal relationship based on the predicate clauses is identified.

8. The method of claim 1, wherein constructing the search query further comprises:

generating predicate clauses based at least in part on the events within the search input; and designating the predicate clauses as inputs to one or more operators, the operator(s) returning a true or false designation depending on whether a specified temporal relationship based on the predicate clauses is identified.

9. The method of claim 1, wherein the search input further specifies inclusion and/or exclusion criteria and wherein solving the one or more constraints against the identified matching patient records comprises applying the inclusion and/or exclusion criteria from the search input.

10. The method of claim 1, wherein solving the constraints comprises determining whether each identified matching patient record includes events having the temporal relationships from the search input.

11. The method of claim 1, wherein the events include one or more of: a diagnosis, a medication, or a lab result.

12. The method of claim 1, wherein the inverted index is constructed from a plurality of de-identified patient records.

13. The method of claim 1, further comprising, after building the index query, enhancing the index query using constraints from the search input, and wherein issuing the index query to the inverted index comprises using the enhanced index query.

14. The method of claim 1, further comprising:

receiving one or more of the patient records;

providing remote access to users over a network so that any one or more of the users can provide at least one updated patient record in real time through an interface, wherein at least one of the users provides an updated patient record in a format other than a common format, wherein the format other than the common format is dependent on hardware and software platform used by the at least one user;

converting the at least one updated patient record into the common format;

generating a plurality of index terms for the at least one updated patient record;

storing the index terms and corresponding matching patient records in a posting list;

generating a set of at least one de-identified record from the at least one updated patient record;

storing the converted at least one updated patient record;

after storing the converted at least one updated patient record, generating a message containing the converted at least one updated patient record; and transmitting the message to one or more users over the network in real time, so that the users have access to the updated patient record.

15. A computer-readable storage medium storing instructions that, when executed by a computing system having a memory and a processor, cause the computing system to perform operations for query patient records, the operations comprising:

receiving a search input that specifies a plurality of events and one or more temporal relationships between the events, wherein the one or more temporal relationships include a temporal relationship that specifies a first event from a first input event set, a second event from a second input event set, wherein the second input event set is different from the first input event set, a maximum time gap between the first event and the second event, and that the first event is the closest previous event from the first input event set to the second event;

constructing a search query from the search input, the search query including an index query and one or more constraints, wherein the index query is based at least in part on the plurality of events within the search input, and the one or more constraints are based at least in part on the one or more temporal relationships from the search input;

executing the index query against an inverted index to identify matching patient records;

solving the one or more constraints against the identified matching patient records; and returning patient records that satisfy the one or more constraints.

16. The computer-readable storage medium of claim 15, the operations further comprising:

receiving a user input including a second search input with a second plurality of events with at least one specified temporal relationship;

generating index terms based on the second plurality of events;

combining the generated index terms into predicate search trees;

combining two or more of the predicate search trees via Boolean operator(s);

generating a multi-clause query based on the combined predicate search trees; and applying the multi-clause query to a corpus of target data to obtain a plurality of matching patient records.

17. The computer-readable storage medium of claim 15, wherein receiving the search input that specifies the plurality of events and one or more temporal relationships between the events comprises receiving one or more temporal constraints between events, the operations further comprising:

decomposing the search input into a first set of logical operations and a second set of logical operations;

based on the first set of logical operations, identifying candidate patient records having the events specified in the search input; and based on the second set of logical operations, filtering the candidate patient records to those patient records that satisfy the temporal constraints specified in the search input.

18. The computer-readable storage medium of claim 15, the operations further comprising:

generating an inverted index for patient records, wherein the generating comprises:

receiving, at a health data platform, a set of patient records from one or more health systems;

processing the set of patient records at the health data platform, wherein the processing includes converting the set of patient records into a common format;

generating a plurality of index terms for each patient record; and storing the index terms and corresponding matching patient records in a posting list.

19. The computer-readable storage medium of claim 15, wherein constructing the search query further comprises generating index terms based on the plurality of events.

20. The computer-readable storage medium of claim 19, wherein constructing the search query further comprises combining a plurality of index terms via one or more Boolean operators.

21. The computer-readable storage medium of claim 15, wherein constructing the search query further comprises:

generating predicate clauses based at least in part on the events within the search input; and designating the predicate clauses as inputs to one or more operators, the operator(s) returning a set of events if a specified temporal relationship based on the predicate clauses is identified.

22. The computer-readable storage medium of claim 15, wherein constructing the search query further comprises:

generating predicate clauses based at least in part on the events within the search input; and designating the predicate clauses as inputs to one or more operators, the operator(s) returning a true or false designation depending on whether a specified temporal relationship based on the predicate clauses is identified.

23. The computer-readable storage medium of claim 15, wherein the search input further specifies inclusion and/or exclusion criteria and wherein solving the one or more constraints against the identified matching patient records comprises applying the inclusion and/or exclusion criteria from the search input.

24. A computing system comprising:

one or more processors;

one or more memories;

a receiving component configured to receive a search input that specifies a plurality of events and one or more temporal relationships between the events, wherein the one or more temporal relationships include a temporal relationship that specifies a first event from a first input event set, a second event from a second input event set, wherein the second input event set is different from the first input event set, a maximum time gap between the first event and the second event, and that the first event is the closest previous event from the first input event set to the second event;

a constructing component configured to construct a search query from the search input, the search query including an index query and one or more constraints, wherein the index query is based at least in part on the plurality of events within the search input, and the one or more constraints are based at least in part on the one or more temporal relationships from the search input;

an execution component configured to execute the index query against an inverted index to identify matching patient records;

a solving component configured to solve the one or more constraints against the identified matching patient records; and a component configured to return patient records that satisfy the one or more constraints, wherein each component comprises computer-executable instructions stored in the one or more memories for execution by the computing system.

25. The computing system of claim 24, wherein the constructing component is further configured to generate index terms based on the plurality of events.

26. The computing system of claim 25, wherein the constructing component is further configured to combine a plurality of index terms via one or more Boolean operators.

27. The computing system of claim 24, wherein the constructing component is further configured to generate predicate clauses based at least in part on the events within the search input and designate the predicate clauses as inputs to one or more operators, the operator(s) returning a set of events if a specified temporal relationship based on the predicate clauses is identified.

28. The computing system of claim 24, wherein constructing component is further configured to generate predicate clauses based at least in part on the events within the search input and designate the predicate clauses as inputs to one or more operators, the operator(s) returning a true or false designation depending on whether a specified temporal relationship based on the predicate clauses is identified.

29. The computing system of claim 24, wherein the search input further specifies inclusion and/or exclusion criteria and wherein solving the one or more constraints against the identified matching patient records comprises applying the inclusion and/or exclusion criteria from the search input.

30. The computing system of claim 24, wherein the solving component is further configured to determine whether each identified matching patient record includes events having the temporal relationships from the search input.

31. The computing system of claim 24, wherein the events include one or more of: a diagnosis, a medication, or a lab result and wherein the inverted index is constructed from a plurality of de-identified patient records.

* * * * *